United States Patent
Connon et al.

(10) Patent No.: US 9,346,755 B2
(45) Date of Patent: *May 24, 2016

(54) KINETIC RESOLUTION

(71) Applicant: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

(72) Inventors: Stephen Joseph Connon, Dublin (IE); Aldo Peschiulli, Lecce (IT); Barbara Procuranti, Marina di Carrara (IT)

(73) Assignee: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN TRINITY COLLEGE, UNIVERSITY OF DUBLIN, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 14/496,157

(22) Filed: Sep. 25, 2014

(65) Prior Publication Data
US 2015/0073170 A1  Mar. 12, 2015

Related U.S. Application Data

(62) Division of application No. 13/515,092, filed as application No. PCT/EP2010/069097 on Dec. 7, 2010, now Pat. No. 8,946,429.

(30) Foreign Application Priority Data

Dec. 9, 2009 (EP) .................................. 09178565

(51) Int. Cl.
C07D 453/04 (2006.01)
C07C 327/22 (2006.01)
C07B 57/00 (2006.01)
C07C 227/32 (2006.01)
C07C 231/18 (2006.01)
C07C 319/02 (2006.01)
C07C 319/12 (2006.01)
C07C 319/28 (2006.01)
C07C 327/28 (2006.01)
C07C 51/083 (2006.01)

(52) U.S. Cl.
CPC ............. C07C 327/22 (2013.01); C07B 57/00 (2013.01); C07C 51/083 (2013.01); C07C 227/32 (2013.01); C07C 231/18 (2013.01); C07C 319/02 (2013.01); C07C 319/12 (2013.01); C07C 319/28 (2013.01); C07C 327/28 (2013.01); C07D 453/04 (2013.01); C07B 2200/07 (2013.01)

(58) Field of Classification Search
CPC .. C07C 319/28; C07C 319/02; C07C 319/12; C07C 231/18; C07C 227/32; C07C 327/28; C07C 327/22; C07C 453/04; C07B 57/00; C07D 453/04

See application file for complete search history.

(56) References Cited

U.S. PATENT DOCUMENTS 8,946,429 B2 * 2/2015 Connon et al. ................ 546/126

FOREIGN PATENT DOCUMENTS

WO 2009/050216 A1 4/2009

OTHER PUBLICATIONS

Brunner, Eur J Org Chem, pp. 2854-2862, 2003.
Vakulya, Am Chem Soc, vol. 7(10), pp. 1967-1969, 2005.
Jiang, Synlett, No. 4. pp. 603-606, 2005.
Nakamura, Adv Synth Catal, vol. 350, pp. 1209-1212, 2008.
Szori, J Mol Cat A: chem, vol. 294, pp. 14-19, 2008.
Faber, Tetrahedron, vol. 50(16), 994775-4794, 1994.
Okino, Org Lett, VOl 6 (4), pp. 625-627, 2004.
Honjo, Takashi et al., "Highly Enantioselective Catalytic Thiolysis of Prochiral Cyclic Dicarboxylic Anhydrides Utilizing a Bifunctional Chiral Sulfonamide", Angewandte Chemie, International Edition (Sep. 4, 2005), vol. 44, No. 36, pp. 5838-5841.
Peschiulli, Aldo et al., "Organocatalytic Asymmetric Addition of Alcohols and Thiols to Activated Electrophiles: Efficient Dynamic Kinetic Resolution and Desymmetrization Protocols", Journal of Organic Chemistry (Jul. 23, 2008), vol. 73, No. 16, pp. 6409-6412.
Chavan, Anil B. et al., "An Efficient Process of Racemization of 3-(Carbamoylmethyl)-5-methylhexanoic acid: A Pregabalin Intermediate", Organic Process Research and Development (May 18, 2009), vol. 13, No. 4, pp. 812-814.
International Search Report dated Mar. 1, 2011 issued in PCT/EP2010/069097.

* cited by examiner

Primary Examiner — D M Seaman
(74) Attorney, Agent, or Firm — Scully, Scott, Murphy & Presser, P.C.

(57) ABSTRACT

While methodologies for the Kinetic Resolution of alcohols are well established, no analogous direct methods exist for the highly selective, direct catalytic Kinetic Resolution of thiols (i.e., R—SH). The present invention relates to a method for resolving stereoisomeric mixtures of thiols. In particular, the present invention relates to purely organocatalytic mediated resolution of enantiomeric mixtures of thiols without the need for enzymes. Also disclosed are some novel catalysts. Such catalysts may comprise a cinchona alkaloid-derived moiety.

18 Claims, 4 Drawing Sheets

KINETIC RESOLUTION

CROSS REFERENCE TO RELATED APPLICATIONS

The present application is a divisional of U.S. patent application Ser. No. 13/515,092 filed on Jun. 11, 2012, which is a 371 of International Patent Application No. PCT/EP2010/069097 filed on Dec. 7, 2010, which claims the benefit of priority of European Patent Application No. 09178565.9 filed on Dec. 9, 2009, the entire contents of which are incorporated by reference.

FIELD OF THE INVENTION

The present invention relates to a method for resolving stereoisomeric mixtures of thiols. In particular, the present invention relates to purely organocatalytic mediated resolution of enantiomeric mixtures of thiols without the need for enzymes. Also disclosed are some novel catalysts.

BACKGROUND TO THE INVENTION

Kinetic resolution (KR) is an established methodology for the preparation of enantioenriched compounds (see Scheme 1). In a chiral environment, for example in the presence of a chiral reagent B*, the enantiomers of a racemic mixture (A and A') exhibit different reaction kinetics making it possible to modify one enantiomer (e.g. to provide A-B*) of the racemic mixture preferentially over the other. Thus, by preferentially modifying one of the enantiomers it is easy to separate it from the other enantiomer.

Scheme 1

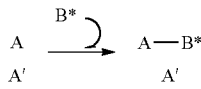

KR represents one of the most convenient methods for the rapid isolation of enantiopure alcohols by resolving the corresponding racemic materials via enantioselective acylation as shown in Scheme 2.

Scheme 2

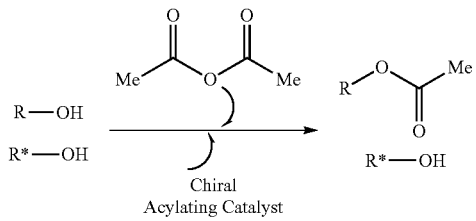

Initially, KR of racemic alcohols was carried out using biological catalysts such as enzymes. However, enzyme mediated catalysis can be troublesome on account of the low tolerance of enzymes to changes in pH and temperature. Furthermore, the incompatibility of enzymes with organic solvents vastly reduces the range of alcohol substrates that are suitable for acylation via enzyme mediated catalysis. Accordingly, in recent years several efficient and selective artificial organocatalysts for these processes have become available. As used herein organocatalysts are small molecule, non-metal containing catalysts that are soluble in organic solvents.

While the KR of alcohols is now a mature and useful technology, no analogous direct methods exist for the highly selective, direct catalytic KR of racemic thiols (i.e., R—SH)—despite the importance of thiols and organosulfur compounds in organic chemistry, and chemical biology.

Baker's yeast has been used to resolve a chiral thiol in the presence of glucose, however the resolved material was isolated in trace amounts only and with low enantioselectivity (40% ee). Reports disclosing lipase-catalysed transesterification of thioesters derived from racemic thiols are also acknowledged. Under optimal conditions the thiol products were obtained with high enantioselectivity (up to 95% ee). However, the latter is a multi-step methodology for the KR of thiols, only three thioester substrates were resolved, the methodology required long reaction times (up to 200 h) and high mass loadings of the enzyme catalyst.

International Patent Publication No. WO2009/050216 discloses a methodology for the dynamic kinetic resolution of thiols comprising utilising a hydrolase enzyme in the presence of an epimerisation catalyst. Notwithstanding these reports, enzymatic mediated resolution of thiols intrinsically suffers from the same problems as enzymatic resolution of alcohols discussed above.

While enantioenriched thiols can be synthesised from the corresponding alcohols, this simply makes one reliant on (and limited by) the availability of the desired alcohol substrate in enantiopure form. In addition, care must be exercised where a substrate (or its derivatives) is capable of racemisation.

For example, in attempting to prepare enantiopure thiols from the corresponding alcohols the present inventors found that subjecting commercially available (R)-1-phenyl-2-methyl-propanol (>99% ee) to a sequence involving mesylation, substitution with thioacetate ion (dry DMSO solvent, rt) and deprotection with $LiAlH_4$ afforded (S)-1-phenyl-2-methyl-propanethiol in a substantially diminished enantiomeric excess of 84.5%, despite considerable care taken to try to avoid conditions favoring a competing SN1 substitution pathway (see Scheme 3).

Scheme 3

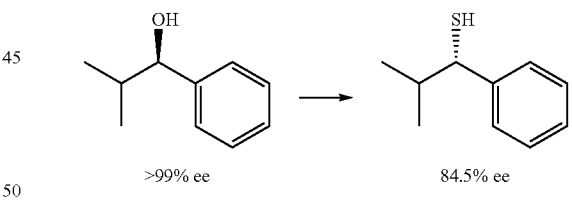

The paucity of methodologies available for the catalytic asymmetric synthesis of enantioenriched thiols, and for the KR of thiols in particular, is attributable to the fact that, relative to alcohols, thiol substrates are inter alia 'softer' nucleophiles, exhibit greater atomic distance between the reacting heteroatom and the stereocenter and possess a lower heteroatom pKa.

Accordingly, it would be desirable to provide an organocatalytic enantioselective acylation protocol for the kinetic resolution of thiols, which mitigates the problems disclosed supra.

SUMMARY OF THE INVENTION

The present invention provides for a method for resolving stereoisomeric mixtures of thiols. In particular, the present invention provides for purely organocatalytic mediated resolution of enantiomeric mixtures of thiols without the need for enzymes. Advantageously, such a method would not suffer from incompatibilities with organic solvents, high/low temperatures, high/low pH, etc. as discussed above.

Accordingly, in a first aspect the present invention provides for a method of resolving a mixture of stereoisomers of a thiol comprising the step of preferentially acylating one thiol stereoisomer in the presence of a bifunctional organocatalyst.

A mixture of stereoisomers of a thiol may comprise either enantiomeric mixtures or diastereomeric mixtures of the thiol. The mixture of stereoisomers of a thiol may be a diastereomeric mixture of the thiol. There is no upper limit on the number of diastereomers in the mixture, for example there could be between four and ten diastereomers within the mixture. The mixture of stereoisomers of a thiol may be an enantiomeric mixture of the thiol, i.e. a mixture consisting of two enantiomers.

As used herein the term mixture does not limit to a two component mix or a specific ratio of two or more components. In particular it does not limit to a 50:50 mixture. Mixture ratios from 1:99 to 99:1 are covered by the term mixture. The term mixture also covers multi component mixtures, such as a mixture of 3 or more diastereomers in any given ratio.

Within this specification, the term bifunctional organocatalyst refers to a chiral, small organic molecule (i.e., non-metal based) having a Lewis acid moiety and a Lewis base moiety within the molecule, which is used in sub-stoichiometric loading relative to at least one of the reactants. The chiral, small organic molecule may comprise between 5 and 60 carbon atoms. The bifunctional organocatalyst may be used in substoichiometric loading relative to the stereoisomeric mixture of the thiol.

Suitably, the bifunctional organocatalyst or chiral small organic molecule is substantially enantiopure. This is important for efficient resolution (or separation) of the mixture of stereoisomers. The bifunctional organocatalyst may function by enhancing the nucleophilicity of a first reaction component and enhancing the electrophilicity of a second reaction component. For example, the bifunctional organocatalyst may enhance the electrophilicity of an acylating agent (such as an organic anhydride) and enhance the nucleophilicity of one enantiomer of an enantiomeric mixture of a thiol, thereby facilitating reaction of both components in a chiral environment.

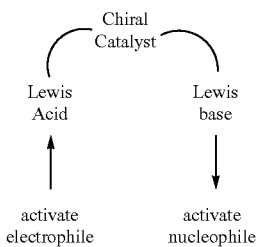

The thiols may be selected from the group consisting of primary thiols and secondary thiols. The thiol may be a thiol selected from the group consisting of $C_1$-$C_{100}$ alkyl, $C_3$-$C_{100}$ cycloalkyl, $C_5$-$C_{100}$ aryl, $C_5$-$C_{100}$ heteroaryl and combinations thereof. The thiol may be a secondary thiol. The secondary thiol may be selected from the group consisting of $C_1$-$C_{100}$ alkyl, $C_3$-$C_{100}$ cycloalkyl, $C_5$-$C_{100}$ aryl, $C_5$-$C_{100}$ heteroaryl and combinations thereof. The secondary thiol may be selected from the group consisting of $C_1$-$C_{20}$ alkyl, $C_5$-$C_{20}$ aryl and combinations thereof. The thiol may be optionally substituted one or more times with at least one of a halogen, $C_1$-$C_5$ alkoxy, $C_1$-$C_5$ thioalkoxy, and cyano.

As used herein, the term "$C_x$-$C_y$ alkyl" embraces $C_x$-$C_y$ unbranched alkyl, $C_x$-$C_y$ branched alkyl and combinations thereof. The term (cyclo)alkyl does not preclude the presence of one or more C—C unsaturated bonds in the carbon (ring)/chain. The terms aryl and heteroaryl encompass fused aromatic and fused heteroaromatic rings respectively.

The method of the present invention may be carried out in a solvent selected from the group consisting of $C_5$-$C_{12}$ hydrocarbons, $C_6$-$C_{12}$ aromatic hydrocarbons, $C_3$-$C_{12}$ ketones (cyclic and acyclic), $C_2$-$C_{12}$ ethers (cyclic and acyclic), $C_2$ to $C_{12}$ esters (cyclic and acyclic), $C_2$-$C_5$ nitriles and combinations thereof. Desirably, the solvent is ethereal. For example, $C_2$-$C_{12}$ ethers (cyclic and acyclic). Suitable ethers may be selected from the group consisting of diethylether, THF, 2-methyl THF, diisopropylether, methyltertbutylether (MTBE) and combinations thereof. In a preferred embodiment, the solvent is methyltertbutylether (MTBE).

The catalyst loading with respect to the thiol may be 0.1-50 mol %, for example 0.1-25 mol %, such as 0.1-10 mol %. Desirably, the catalyst loading with respect to the thiol is 5-10 mol %. Advantageously, this represents a highly economic and efficient catalyst loading.

The bifunctional organocatalyst may comprise a cinchona alkaloid. As used herein a catalyst comprising a cinchona alkaloid refers to any catalyst comprising one of the following structural elements:

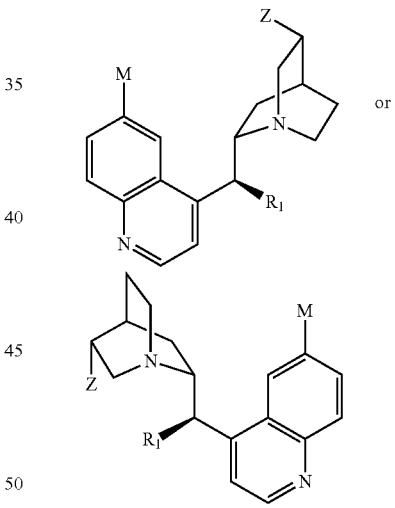

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe; and $R_1$ is a moiety comprising a hydrogen bond donor.

The moiety comprising a hydrogen bond donor may comprise between 1 and 30 carbon atoms. The cinchona alkaloid may be substituted with a urea, thiourea or sulfonamide functional group. For example, $R_1$ may comprise a urea, thiourea or sulfonamide functional group. For example, $R_1$ may comprise a $C_1$-$C_{20}$ urea, $C_1$-$C_{20}$ thiourea or a $C_1$-$C_{20}$ sulfonamide.

The bifunctional organocatalyst may be selected from the group consisting of:

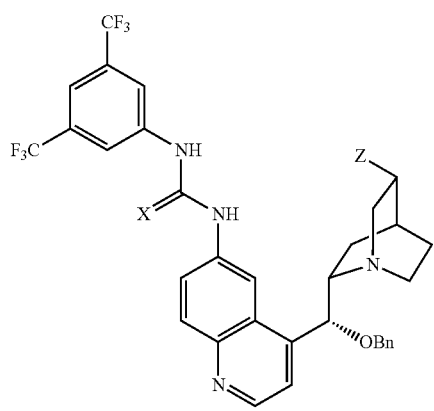
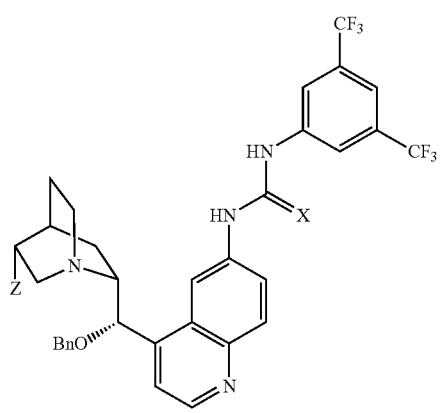
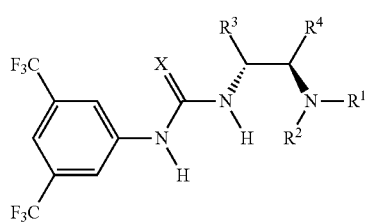
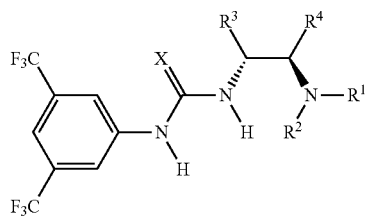
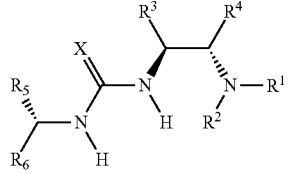
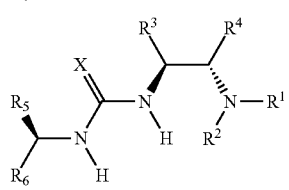
-continued
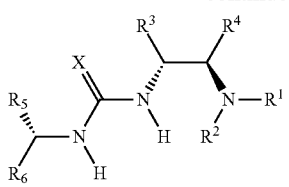
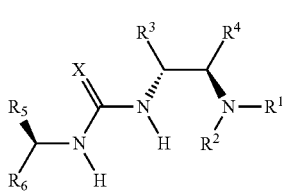
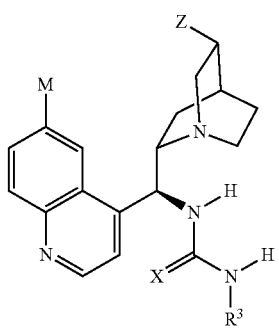
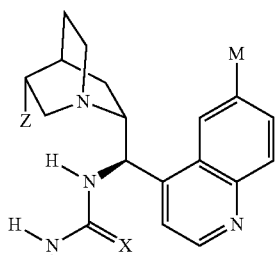
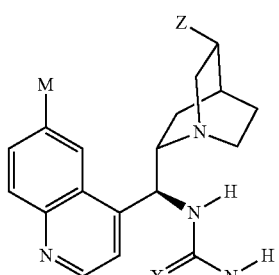
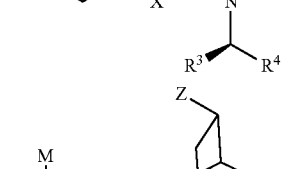
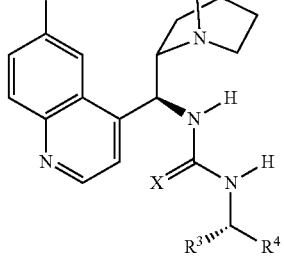

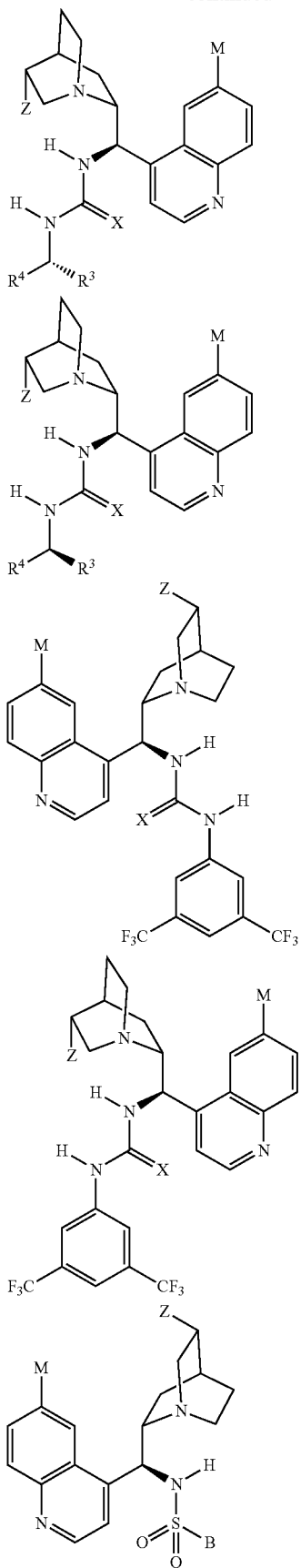

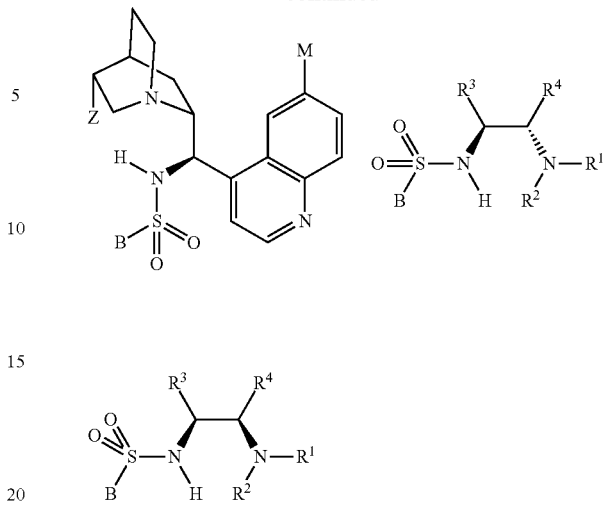

wherein X can be O or S;

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_1$ and $R_2$ can be the same or different and may comprise $C_1$-$C_{15}$ alkyl, or $R_1$ and $R_2$ may together define a $C_3$-$C_{15}$ cycloalkyl ring (i.e., $R_1$ and $R_2$ may together with N define a $C_3$-$C_{15}$ heterocyclic ring), wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_3$ and $R_4$ can be the same or different and may comprise $C_1$-$C_{15}$ alkyl, or $R_3$ and $R_4$ may together define a $C_3$-$C_{15}$ cycloalkyl ring, a $C_5$-$C_{15}$ aryl ring, or a $C_5$-$C_{15}$ heteroaryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_5$ and $R_6$ can be the same or different and may comprise $C_1$-$C_{15}$ alkyl, or $R_5$ and $R_6$ may together define a $C_3$-$C_{15}$ cycloalkyl ring, a $C_5$-$C_{15}$ aryl ring, or a $C_5$-$C_{15}$ heteroaryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

As used herein "Bn" is short hand for "benzyl".

The bifunctional organocatalyst may be selected from the group consisting of:

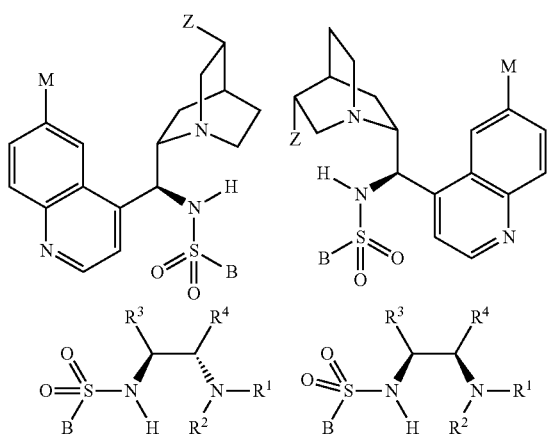

wherein Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_1$ and $R_2$ can be the same or different and may comprise $C_1$-$C_{15}$ alkyl, or $R_1$ and $R_2$ may together define a $C_3$-$C_{15}$ cycloalkyl ring (i.e., $R_1$ and $R_2$ may together with N define a $C_3$-$C_{15}$ heterocyclic ring), wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_3$ and $R_4$ can be the same or different and may comprise $C_1$-$C_{15}$ alkyl, or $R_3$ and $R_4$ may together define a $C_3$-$C_{15}$ cycloalkyl ring, a $C_5$-$C_{15}$ aryl ring, or a $C_5$-$C_{15}$ heteroaryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

B may be $C_5$-$C_{15}$ aryl, or $C_5$-$C_{15}$ heteroaryl optionally substituted one or more times with at least one of a halogen, $C_1$-$C_5$ alkyl, or combinations thereof.

The bifunctional organocatalyst may be selected from the group comprising:

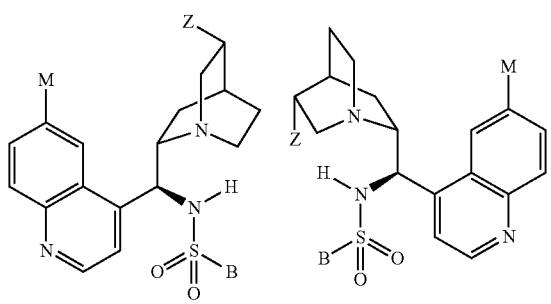

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe; and

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

B may be $C_5$-$C_{15}$ aryl, or $C_5$-$C_{15}$ heteroaryl optionally substituted one or more times with at least one of a halogen, $C_1$-$C_5$ alkyl, or combinations thereof.

According to the method of the present invention the step of acylating the thiol comprises reacting the thiol with an organic anhydride. The organic anhydride may be a cyclic anhydride. The organic anhydride (cyclic or acyclic) may be a $C_4$-$C_{50}$ organic anhydride.

The organic anhydride may be selected from the group consisting of:

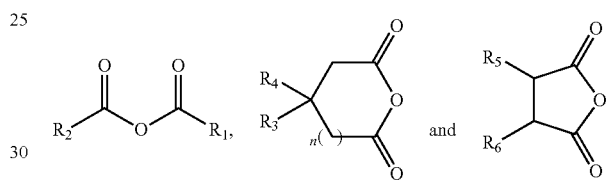

wherein $R_1$ and $R_2$ are the same or different and are selected from the group consisting of $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl;

$R_3$ and $R_4$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl, such that at least one of $R_3$ and $R_4$ is H;

$R_5$ and $R_6$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl; and n can be 0-5.

The organic anhydride may be of the general formula:

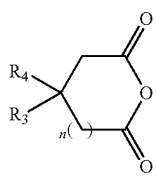

and may be a prochiral anhydride, wherein $R_3$ and $R_4$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl, such that at least one of $R_3$ and $R_4$ is H; and n is 1.

According to the method of the present invention acylation of the thiol with the prochiral anhydride in the presence of the bifunctional organocatalyst may proceed with desymmetrisation of the prochiral anhydride to afford a thioester. The thioester may be at least one of enantiomerically or diastereomerically enriched.

The organic anhydride may be of the general formula:

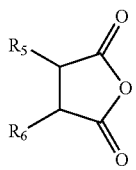

and may be a meso anhydride, wherein $R_5$ and $R_6$ are the same and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl.

According to the method of the present invention acylation of the thiol with the meso anhydride in the presence of the bifunctional organocatalyst may proceed with desymmetrisation of the meso anhydride to afford a thioester. The thioester may be at least one of enantiomerically or diastereomerically enriched.

In a further aspect, the present invention provides for use of the method of the present invention in the preparation of an enantioenriched thiol. The enantioenriched thiol may be a pharmaceutical. For example, the method of the present invention may be used in the preparation of enantioenriched 3-(aminomethyl)-5-methylhexanoic acid. The (R)-enantiomer of 3-(aminomethyl)-5-methylhexanoic acid is the blockbuster anti-convulsive drug Pregabalin marketed as 'Lyrica'®.

In yet a further aspect the present invention provides for a process for the preparation of enantioenriched 3-(aminomethyl)-5-methylhexanoic acid comprising the steps of:

preferentially acylating one thiol enantiomer of an enantiomeric mixture of the thiol with 3-isobutylglutaric anhydride in the presence of a bifunctional organocatalyst according to the method of the present invention; and converting the thioester functional group (formed in the previous step) into an amine.

The step of converting the thioester functional group into an amine may comprise:

i) aminolysis of the thioester functional group to yield an amide; and ii) subjecting the amide product of step i) to a Hofmann rearrangement.

Aminolysis of the thioester functional group may comprise treating the thioester with ammonia or an amine. Preferably, aminolysis of the thioester functional group comprises treating the thioester with ammonia to yield a primary amide. The Hofmann rearrangement is an eminent synthetic transformation which converts an amide to an amine with the loss of carbon monoxide. All protocols for effecting this transformation are embraced by the present invention.

The invention further provides for a compound having the general structure:

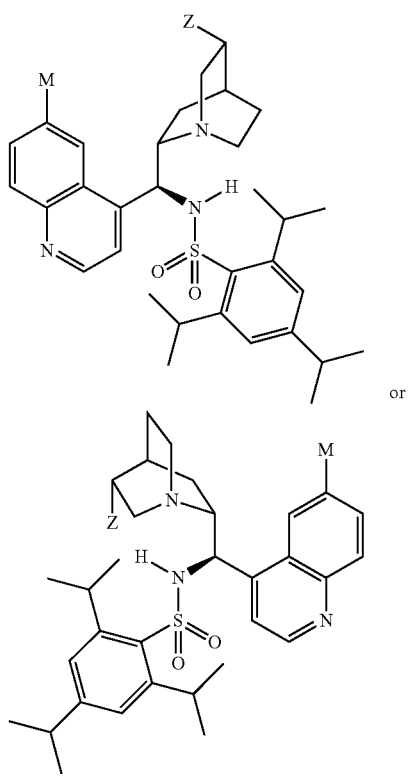

or

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof; and M can be H, OH, or OMe.

The compound of the present invention may be used as an acylation catalyst in the resolution of a mixture of stereoisomers of a thiol. That is a molecule that catalyses preferential acylation of one thiol stereoisomer over another thiol stereoisomer. Desirably, the mixture of stereoisomers of a thiol is an enantiomeric mixture of the thiol.

In a further aspect the present invention provides for a method of desymmetrising at least one of a prochiral anhydride or a meso anhydride comprising the steps of:

(i) adding the prochiral anhydride or meso anhydride to a mixture of enantiomeric thiols; and (ii) adding a bifunctional organocatalyst to the mixture of the prochiral anhydride and the enantiomeric thiols.

The prochiral anhydride may be a $C_6$-$C_{40}$ anhydride. The meso anhydride may be a $C_6$-$C_{40}$ anhydride. The prochiral anhydride may be of the general formula:

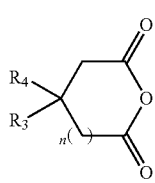

wherein $R_3$ and $R_4$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl, such that at least one of $R_3$ and $R_4$ is H; and n is 1.

The meso anhydride may be of the general formula:

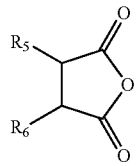

wherein $R_5$ and $R_6$ are the same and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of a halogen, cyano, or $C_1$-$C_5$ fluoroalkyl.

The thiols may be selected from the group consisting of primary thiols and secondary thiols. The thiol may be a thiol selected from the group consisting of $C_1$-$C_{100}$ alkyl including $C_3$-$C_{100}$ cycloalkyl, $C_5$-$C_{100}$ aryl including $C_5$-$C_{100}$ heteroaryl and combinations thereof. The thiol may be a secondary thiol. The secondary thiol may be selected from the group consisting of $C_1$-$C_{100}$ alkyl including $C_3$-$C_{100}$ cycloalkyl, $C_5$-$C_{100}$ aryl including $C_5$-$C_{100}$ heteroaryl and combinations thereof. The secondary thiol may be selected from the group consisting of $C_1$-$C_{20}$ alkyl, $C_5$-$C_{20}$ aryl and combinations thereof. The thiol may be optionally substituted one or more times with at least one of a halogen, $C_1$-$C_5$ alkoxy, $C_1$-$C_5$ thioalkoxy, and cyano.

The bifunctional organocatalyst may comprise a cinchona alkaloid. For example, the catalyst may comprise one of the following structural elements:

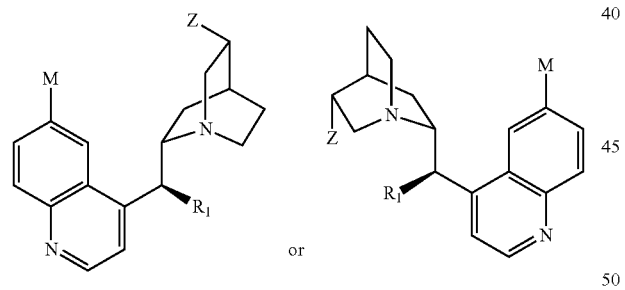

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe; and $R_1$ is a moiety comprising a hydrogen bond donor.

The moiety comprising a hydrogen bond donor may comprise between 1 and 30 carbon atoms. The cinchona alkaloid may be substituted with a urea, thiourea or sulfonamide functional group. For example, $R_1$ may comprise a urea, thiourea or sulfonamide functional group. For example, $R_1$ may comprise a $C_1$-$C_{20}$ urea, $C_1$-$C_{20}$ thiourea or a $C_1$-$C_{20}$ sulfonamide.

The bifunctional organocatalyst may be selected from the group consisting of:

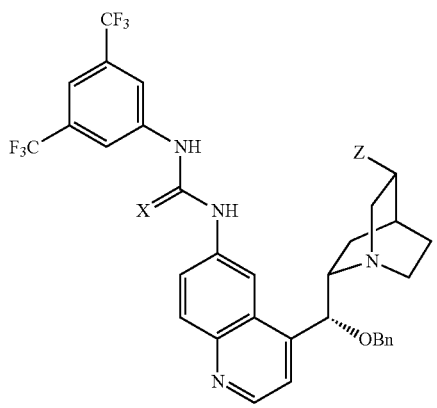

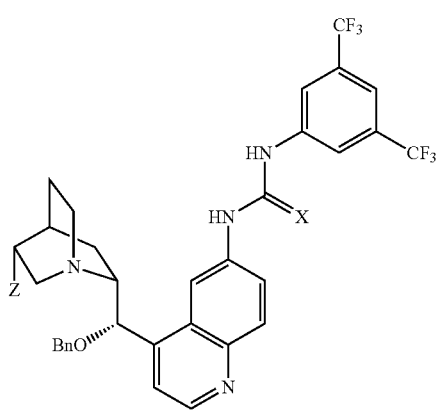

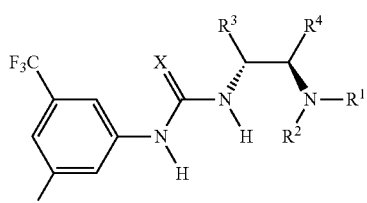

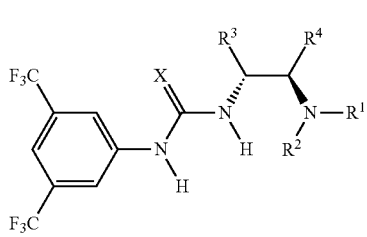

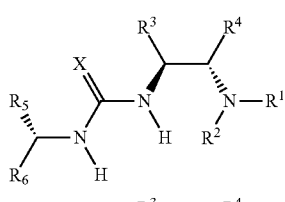

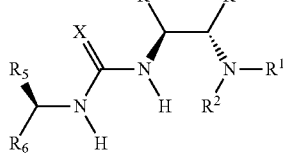

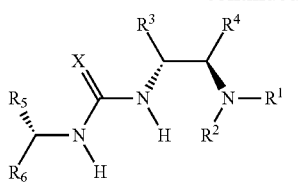
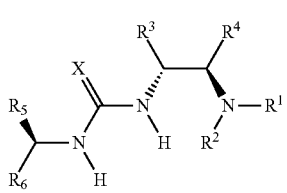
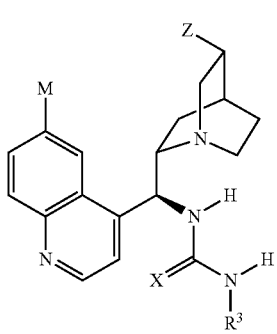
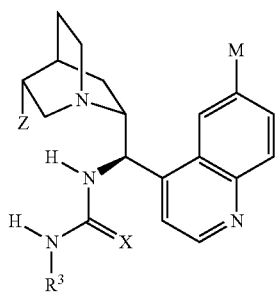
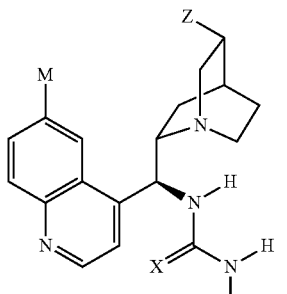
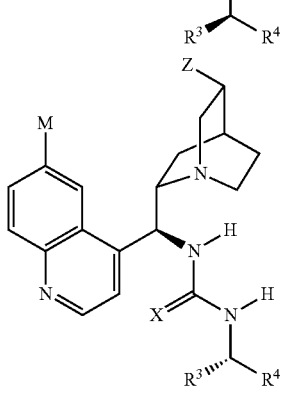
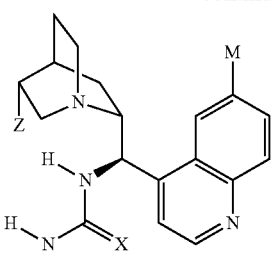
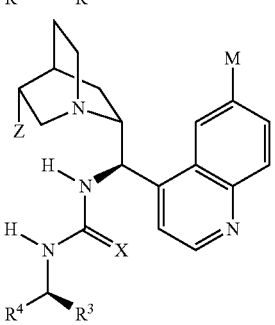
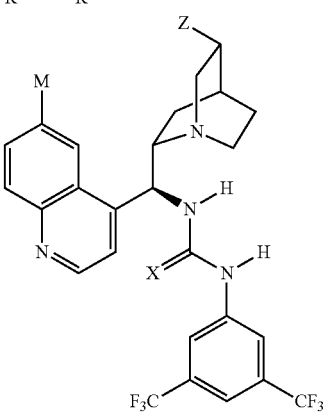
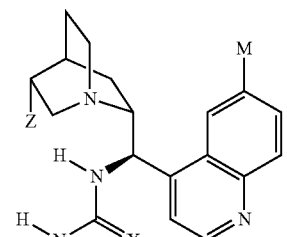
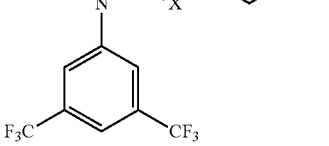
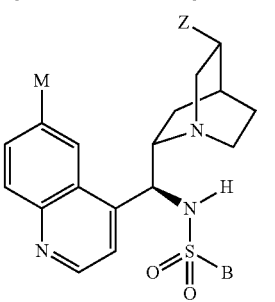

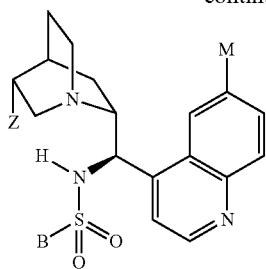

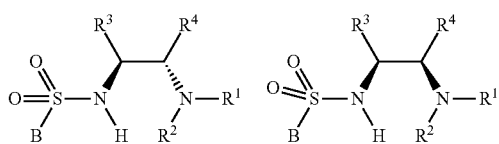

wherein X can be O or S;

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_1$ and $R_2$ can be the same or different and may comprise $C_1$-$C_{15}$ alkyl, or $R_1$ and $R_2$ may together define a $C_3$-$C_{15}$ cycloalkyl ring (i.e., $R_1$ and $R_2$ may together with N define a $C_3$-$C_{15}$ heterocyclic ring), wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_3$ and $R_4$ can be the same or different and may comprise $C_1$-$C_{15}$ alkyl, or $R_3$ and $R_4$ may together define a $C_3$-$C_{15}$ cycloalkyl ring, a $C_5$-$C_{15}$ aryl ring, or a $C_5$-$C_{15}$ heteroaryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_5$ and $R_6$ can be the same or different and may comprise $C_1$-$C_{15}$ alkyl, or $R_5$ and $R_6$ may together define a $C_3$-$C_{15}$ cycloalkyl ring, a $C_5$-$C_{15}$ aryl ring, or a $C_5$-$C_{15}$ heteroaryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

The bifunctional organocatalyst may be selected from the group consisting of:

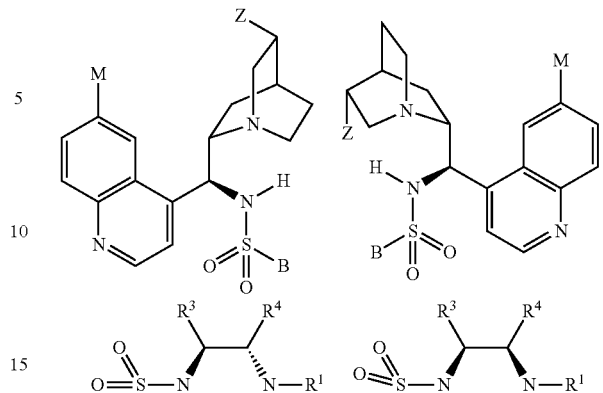

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_1$ and $R_2$ can be the same or different and may comprise $C_1$-$C_{15}$ alkyl, or $R_1$ and $R_2$ may together define a $C_3$-$C_{15}$ cycloalkyl ring (i.e., $R_1$ and $R_2$ may together with N define a $C_3$-$C_{15}$ heterocyclic ring), wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof; and $R_3$ and $R_4$ can be the same or different and may comprise $C_1$-$C_{15}$ alkyl, or $R_3$ and $R_4$ may together define a $C_3$-$C_{15}$ cycloalkyl ring, a $C_5$-$C_{15}$ aryl ring, or a $C_5$-$C_{15}$ heteroaryl ring wherein each may be optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

B may be $C_5$-$C_{15}$ aryl, or $C_5$-$C_{15}$ heteroaryl optionally substituted one or more times with at least one of a halogen, $C_1$-$C_5$ alkyl, or combinations thereof.

The bifunctional organocatalyst may be selected from the group comprising:

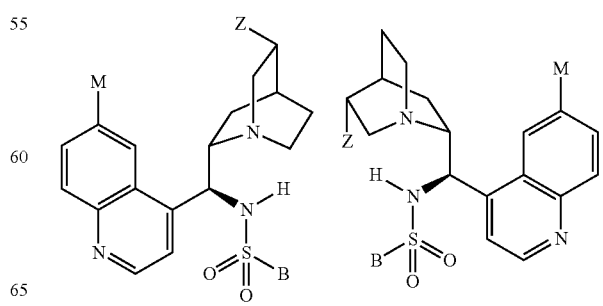

Z can be a $C_1$ to $C_5$ carbon chain optionally comprising at least one C—C unsaturated bond, and optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe; and

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of a halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

B may be $C_5$-$C_{15}$ aryl, or $C_5$-$C_{15}$ heteroaryl optionally substituted one or more times with at least one of a halogen, $C_1$-$C_5$ alkyl, or combinations thereof.

The method of the present invention may be carried out in a solvent selected from the group consisting of $C_5$-$C_{12}$ hydrocarbons, $C_6$-$C_{12}$ aromatic hydrocarbons, $C_3$-$C_{12}$ ketones (cyclic and acyclic), $C_2$-$C_{12}$ ethers (cyclic and acyclic), $C_2$ to $C_{12}$ esters (cyclic and acyclic), $C_2$-$C_5$ nitriles and combinations thereof. Desirably, the solvent is ethereal. For example, $C_2$-$C_{12}$ ethers (cyclic and acyclic). Suitable ethers may be selected from the group consisting of diethylether, THF, 2-methyl THF, diisopropylether, methyltertbutylether (MTBE) and combinations thereof. In a preferred embodiment, the solvent is methyltertbutylether (MTBE).

The catalyst loading with respect to the thiol may be 0.1-50 mol %, for example 0.1-25 mol %, such as 0.1-10 mol %. Desirably, the catalyst loading with respect to the thiol is 5-10 mol %. This represents a highly economic and efficient catalyst loading.

The compounds resolved by the present invention may be found or isolated in the form of esters, salts, hydrates or solvates—all of which are embraced by the present invention.

Where suitable, it will be appreciated that all optional and/or preferred features of one embodiment of the invention may be combined with optional and/or preferred features of another/other embodiment(s) of the invention.

BRIEF DESCRIPTION OF THE DRAWINGS

Additional features and advantages of the present invention are described in, and will be apparent from, the detailed description of the invention and from the drawings in which.

DETAILED DESCRIPTION OF THE INVENTION

Figure 1:
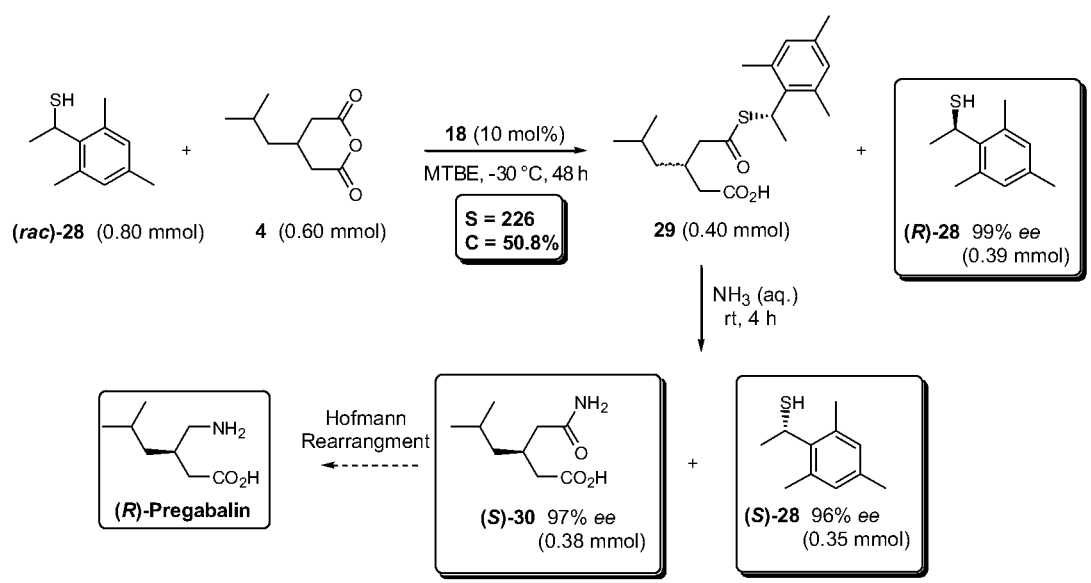
FIG. 1 illustrates Kinetic Resolution of a thiol with simultaneous enantioselective synthesis of a (R)-Pregabalin precursor.
Figure 2:
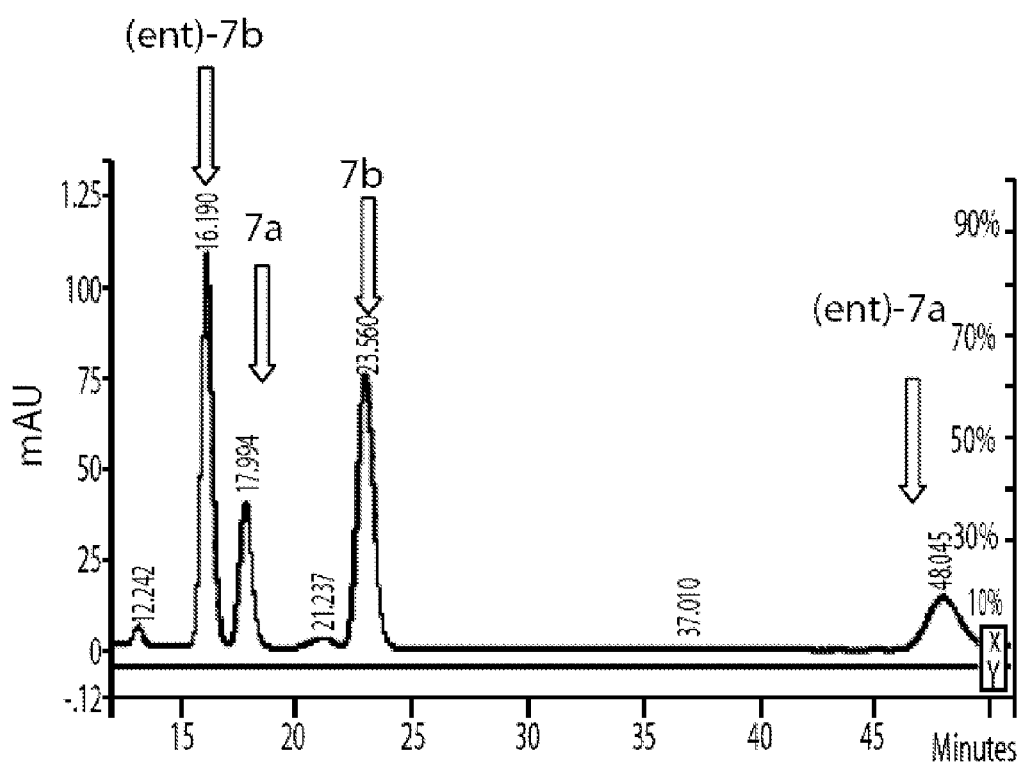
FIG. 2 depicts a chromatogram of the thioesters 7a-b (derivatised as their o-nitrophenyl esters for analysis via CSP-HPLC) from the reaction of 1 with 3 in the presence of triethylamine and an achiral thiourea as catalysts.
Figure 3:
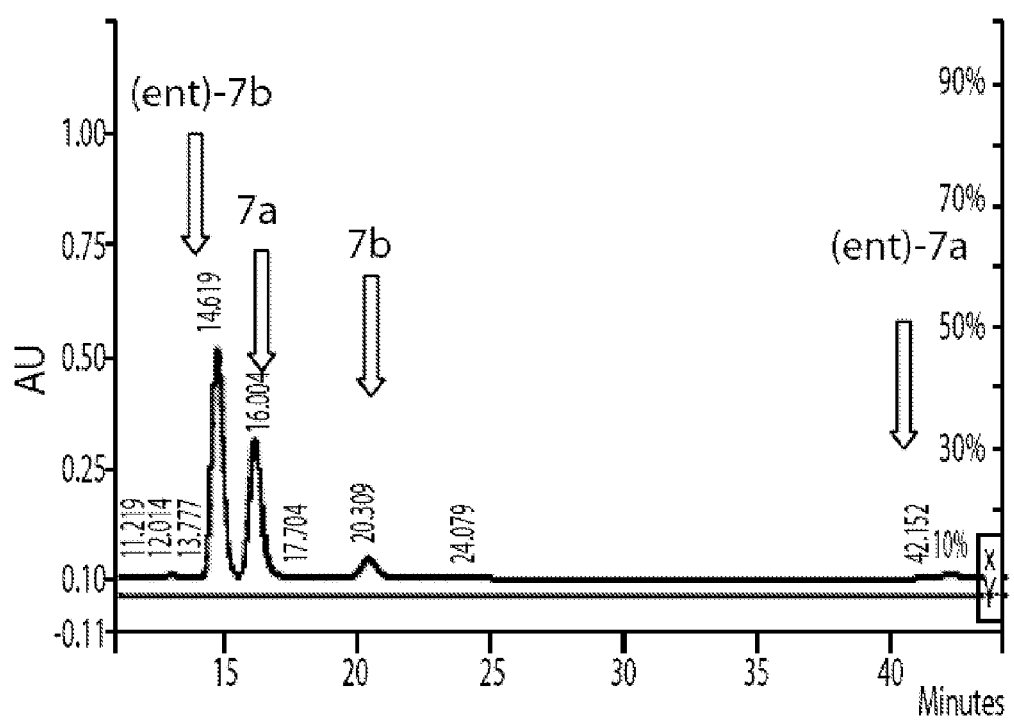
FIG. 3 depicts a chromatogram of the thioesters 7a-b (derivatised as their o-nitrophenyl esters for analysis via CSP-HPLC) from the reaction of (S)-1 (84.5% ee) with 3 in the presence of triethylamine and an achiral thiourea as catalysts.
Figure 4:
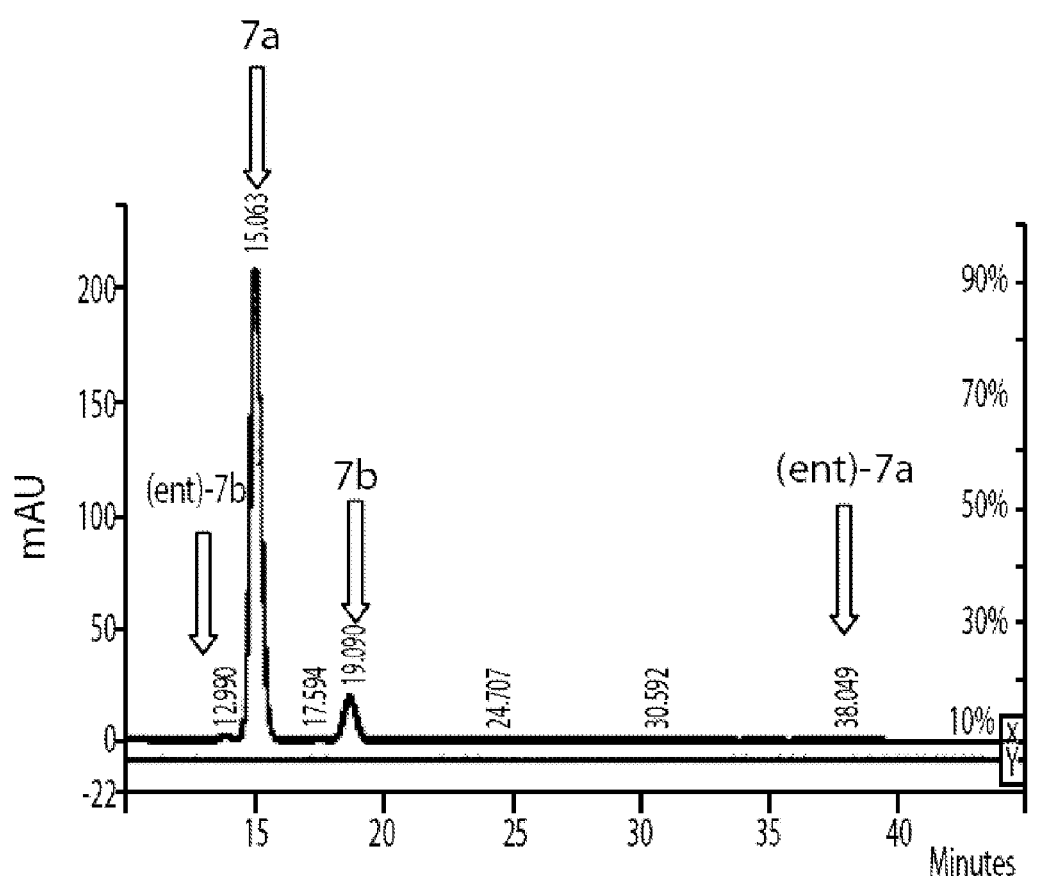
FIG. 4 depicts a chromatogram of the thioesters 7a-b (derivatised as their o-nitrophenyl esters for analysis via CSP-HPLC) from the reaction of 1 with 3 in the presence of catalyst 18 in MTBE at −30° C.

It should be readily apparent to one of ordinary skill in the art that the examples disclosed herein below represent generalised examples only, and that other arrangements and methods capable of reproducing the invention are possible and are embraced by the present invention.

Preliminary experiments related to the acylative KR of the racemic sec-thiol 1 with glutaric anhydride (2a) in the presence of bifunctional (thio)urea-derived organocatalysts 10-12 and sulphonamide 13 (Table 1). Initial results were far from encouraging—acylation proceeded smoothly at low catalyst loading (5 mol %), but resulted in products of low enantiomeric excess (entries 1-4). Of the four catalysts tested sulphonamide 13 proved superior to the (thio)urea-derivatives and could promote the KR with a very modest selectivity ($k_{fast}/k_{slow}$) of 1.5 (13% ee at 50% conv., entry 4). Further experimentation identified methyl tert-butylether (MTBE) as the optimal solvent overall, although the KR of 1 was slower but more selective in THF (entries 4-7).

These results represented the first examples of direct catalytic asymmetric KR of a thiol. Subsequently, KR reactions using 3-substituted achiral anhydride electrophiles 3a-5 were tried. This complicated matters considerably, as now control over the formation of 4 possible thioester diastereomers is required. In addition, it allowed for the possibility of a conceptually novel type of catalytic process where both kinetic resolution and anhydride desymmetrisation occur simultaneously. Gratifyingly, this proved to be the case—use of anhydrides 3a-5 resulted in more enantioselective acylations (entries 8-11), with methyl glutaric anhydride (3a) proving optimal. Using this electrophile the resolved thiol could be isolated in 33% ee at 50% conversion (using either 1 or 5 mol % of catalyst 13), corresponding to S=2.7.

Product esters 7a and 7b were both formed with excellent enantioselectivity (>90% ee) and with encouraging diastereocontrol (67:33 dr, entry 8). With respect to the anhydride, the desymmetrisation aspect of the reaction was highly selective—the parameter $ee_{desymm}$ (Table 1) represents the percentage excess of products derived from attack of the thiol 1 at one prochiral anhydride carbonyl moiety over the other (i.e. the enantiomeric excess of the desymmetrised product if the combined thioester diastereomers were substituted by an achiral (non-hydroxide) nucleophile without racemisation). It is also noteworthy that in the presence of triethylamine as an achiral catalyst the diastereoselectivity is reversed, with 19 as the major diastereomer.

Next the steric and electronic characteristics of the catalyst were systematically varied through the synthesis and evaluation of sulfonamides 14-17. While the electron deficient pentafluorophenyl-substituted catalyst fared a little better than 13, less acidic analogues 15-17 respectively possessed enhanced selectivity profiles (entries 12-15). Given the superiority of the hindered promoter 16, it was decided to accentuate the steric bulk of the sulfonamide further via the synthesis of the novel catalyst 18, which proved almost as active as 13 yet promoted the acylation with a synthetically useful KR selectivity of 8.5 (entry 16). Further optimisation of the reaction conditions (entries 17-19) resulted in the KR of thiol 1 with outstanding selectivity (S=25.5)—allowing the isolation of resolved (R)-1 in 90% ee at 54% conversion, along with ester 7a (formed as the major diastereomer, 89:11 dr) in 98% ee, with an excellent attendant $ee_{desymm}$ of 96% (entry 19).

TABLE 1

Kinetic resolution of thiol 1 with simultaneous desymmetrisation of achiral-anhydrides 3-5

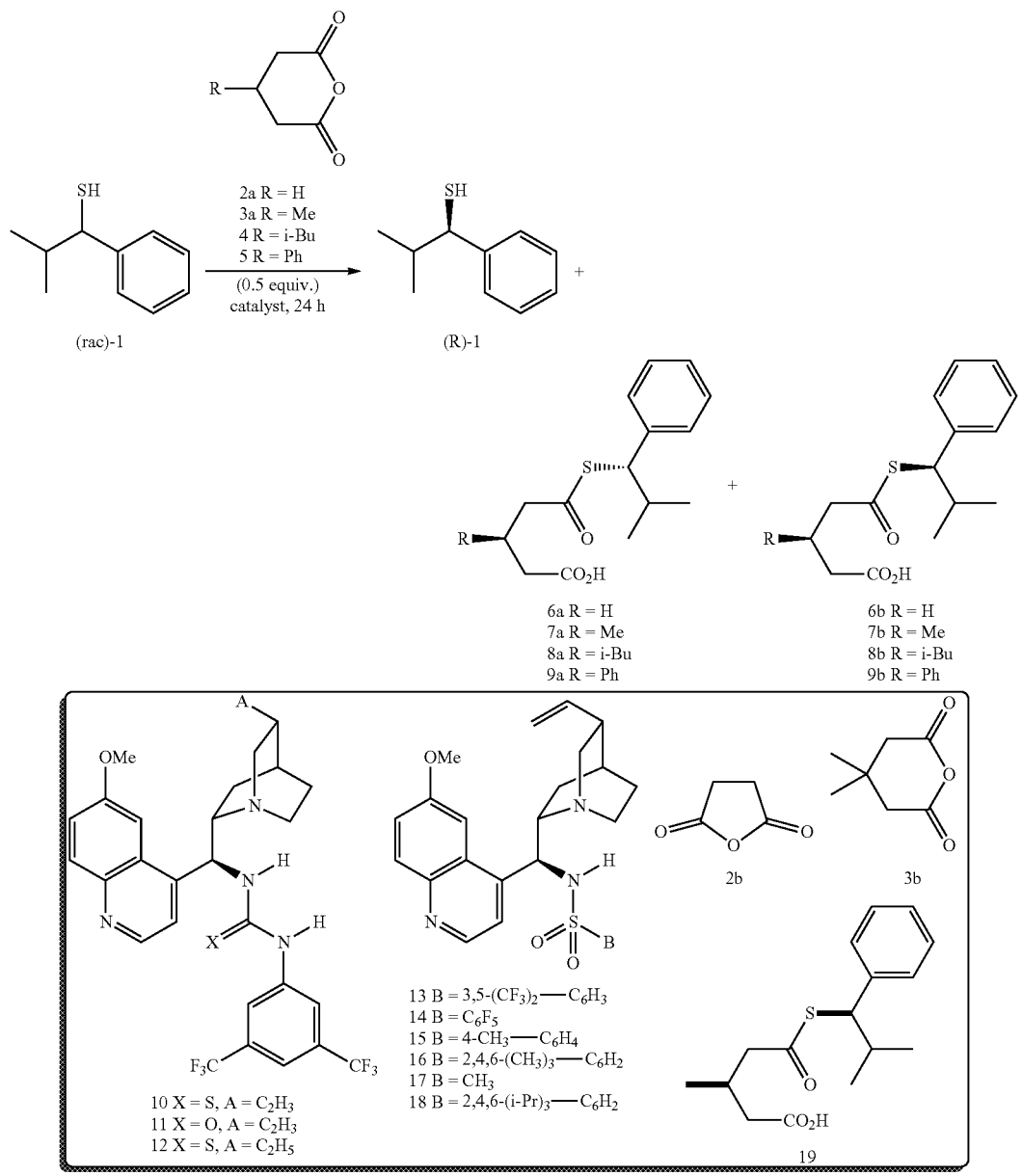

| entry | anhydride (equiv.) | catalyst (mol %) | solvent | T (°C.) | conv. (%)[c] | dr[d] | ee$_{esterA}$ (%)[e] | ee$_{esterB}$ (%)[e] | ee$_{desym}$ (%)[e,f] | ee$_{thiol}$ (%)[e] | S[g] |
|---|---|---|---|---|---|---|---|---|---|---|---|
| 1 | 2a (0.5) | 10 (5) | MTBE | rt | 49 | — | 6.5 | — | — | 7 | 1.2 |
| 2 | 2a (0.5) | 11 (5) | MTBE | rt | 50 | — | 9 | — | — | 9 | 1.3 |
| 3 | 2a (0.5) | 12 (5) | MTBE | rt | 50 | — | 6 | — | — | 6 | 1.2 |
| 4 | 2a (0.5) | 13 (5) | MTBE | rt | 50 | — | 13 | — | — | 13 | 1.5 |
| 5 | 2a (0.5) | 13 (5) | Et$_2$O | rt | 50 | — | 14 | — | — | 14 | 1.5 |
| 6 | 2a (0.5) | 13 (5) | THF | rt | 39 | — | 27 | — | — | 17 | 2.1 |
| 7 | 2a (0.5) | 13 (5) | CH$_2$Cl$_2$ | rt | 16 | — | n.d. | — | — | — | — |
| 8 | 3a (0.5) | 13 (5) | MTBE | rt | 50 | 66.5:33.5 | 95 | 91 | 92 | 33 | 2.7 |
| 9 | 3a (0.5) | 13 (1) | MTBE | rt | 49 | 67:33 | 97 | 88 | 94 | 33 | 2.7 |
| 10 | 4 (0.5) | 13 (5) | MTBE | rt | 50 | n.d. | n.d. | n.d. | n.d. | 21 | 1.8 |
| 11 | 5 (0.5) | 13 (5) | MTBE | rt | 50 | 60:40 | n.d. | n.d. | n.d. | 26 | 2.3 |
| 12 | 3a (0.5) | 14 (5) | MTBE | rt | 49 | 70:30 | 97 | 87 | 94 | 41 | 3.9 |
| 13 | 3a (0.5) | 15 (5) | MTBE | rt | 47 | 73:27 | 97 | 93 | 96 | 41 | 4.0 |
| 14 | 3a (0.5) | 16 (5) | MTBE | rt | 44 | 79:21 | 97 | 90 | 96 | 45 | 5.6 |
| 15 | 3a (0.5) | 17 (5) | MTBE | rt | 48 | 75:25 | 95 | 84 | 92 | 44 | 4.3 |
| 16 | 3a (0.5) | 18 (5) | MTBE | rt | 48 | 89:11 | 95 | 68 | 90 | 60 | 8.5 |
| 17[a] | 3a (0.5) | 18 (5) | MTBE | 0 | 43 | 89:11 | 98 | 78 | 96 | 58 | 13.6 |

TABLE 1-continued

| | | | | | | | | | | | | |
|---|---|---|---|---|---|---|---|---|---|---|---|---|
| 18[a] | 3a (0.75) | 18 (10) | MTBE | 0 | 62 | 79:21 | 95 | 90 | 94 | 93 | | 11.6 |
| 19[b] | 3a (0.75) | 18 (10) | MTBE | −30 | 54 | 89:11 | 98 | 84 | 96 | 90 | | 25.5 |
| 20[b] | 2b (0.75) | 18 (10) | MTBE | −30 | 33 | — | n.d. | — | — | 42 | (85)[h] | 17.9 |
| 21[b] | 3b (0.75) | 18 (10) | MTBE | −30 | 4 | — | n.d. | — | — | n.d. | | n.d. |
| 22[b] | 2a (0.75) | 18 (10) | MTBE | −30 | 50 | — | n.d. | — | — | 68 | (68)[h] | 10.7 |

[a]48 h.
[b]72 h.
[c]Conversion was determined using CSP-HPLC, where conversion = 100 × $ee_{thiol}/(ee_{thiol} + ee_{thioester})$; the value of $ee_{thioester}$ was calculated using all four thioester stereoisomers.
[d]Diastereomeric ratio = (6-9a + ent-6-9a):(6-9b + ent-6-9b).
[e]Determined by CSP-HPLC, see supporting information.
[f]Desymmetrisation efficiency: the enantiomeric excess of the desymmetrised product if the combined thioester products were substituted by an achiral (non-hydroxide) nucleophile, calculated as 100 × [(6-9a + 6-9b) − (ent-6-9a + ent-6-9b)]/[(6-9a + 6-9b) +(ent-6-9a + ent-6-9b)].
[g]S = enantioselectivity ($k_{fast}/k_{slow}$).
[h]Value in parenthesis refers to the ee of the thiol obtained after deprotection via cleavage of the combined thioester products.

Thus, under optimum conditions 18 is capable of mediating the highly efficient and selective KR of a substrate class previously outside the orbit of direct enantioselective catalytic acylation, with the simultaneous desymmetrisation of a synthetically useful class of inexpensive achiral anhydride acylating agent—also with excellent enantioselectivity. To demonstrate that the desymmetrisation and kinetic resolution processes are synergistic, we next carried out the process under optimum conditions using the non-prochiral anhydrides 2a, 2b and 3b (entries 20-22). Kinetic resolution was either too slow or proceeded with lower enantioselectivity using these electrophiles.

Attention now turned to the question of substrate scope (Table 2). It was found that variation of the steric bulk of both the aromatic and aliphatic substituent is well tolerated by the catalyst—for example, α-Me, -Et, -$^i$Pr and -$^t$Bu derivatives of benzyl mercaptan (i.e. 1 and 20-22, entries 1-4) could be resolved with excellent selectivity (up to S>50), resulting in the isolation of the unreacted thiol with >90% ee at ca. 50% conversion. A strong correlation between increasing aliphatic substituent bulk and selectivity was observed; however it is noteworthy that even the challenging substrate 20 (where the steric discrepancy between the two carbon-based substituents is smallest) could be resolved with synthetically useful selectivity. Variation of the characteristics of the aromatic substituent produced interesting results—substitution in the para-position either slightly reduces or has no impact on enantioselectivity (23-25, entries 5-7), while steric bulk at the ortho-position dramatically improved the KR; in optimum cases this resulted in levels of enantiodiscrimination (S>>100) more usually associated with the enzymatic KR of alcohols (26-28, entries 8-12).

Synthesis of Pregabalin
[(R)-3-(aminomethyl)-5-methylhexanoic acid]

To demonstrate the potential utility of this methodology, the KR of thiol 28 (0.80 mmol) was carried out with catalyst 18 in the presence of achiral anhydride 4, which furnished (R)-28 (0.39 mmol, 99% ee) and the ring-opened product 29 (0.40 mmol) with excellent efficiency at 51% conversion as shown in FIG. 1. Thioester 29 (as a mixture of diastereomers) was then treated with aqueous ammonia, resulting in its cleavage to afford the other thiol enantiomer (S)-28 (96% ee, 0.35 mmol) and the aminolysed product (S)-30 (97% ee, 0.38 mmol), again with high efficiency. Hemiamide (S)-30 is a precursor which can be converted in a single step to the (R)-antipode of the anticonvulsive agent Pregabalin and thus this sequence—in addition to serving as a highly efficient KR of 28—constitutes a rapid and convenient formal synthesis of the 'blockbuster' drug (marketed as 'Lyrica'®).

TABLE 2

Evaluation of substrate scope

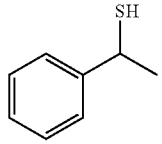

| entry | substrate | X | time (h) | conv. (%)[a] | ee$_{thiol}$ (%)[b] | S[c] | abs. config.[d] |
|---|---|---|---|---|---|---|---|
| 1 | 20 | 0.75 | 68 | 63 | 97 | 14.5 | (R) |

TABLE 2-continued

Evaluation of substrate scope

| entry | substrate | X | time (h) | conv. (%)[a] | ee$_{thiol}$ (%)[b] | S[c] | abs. config.[d] |
|---|---|---|---|---|---|---|---|
| 2 | 21 (1-phenylpropyl SH) | 0.75 | 74 | 56 | 91 | 19.0 | (R) |
| 3[e] | 1 (1-phenyl-2-methylpropyl SH) | 0.75 | 68 | 54 | 90 | 25.5 | (R) |
| 4[f] | 22 (1-phenyl-2,2-dimethylpropyl SH) | 0.75 | 96 | 52 | 94 | 51.5 | (R) |
| 5 | 23 (1-(4-chlorophenyl)ethyl SH) | 0.75 | 72 | 65 | 95 | 10.7 | (R) |
| 6 | 24 (1-(4-methoxyphenyl)ethyl SH) | 0.90 | 120 | 56 | 87 | 15.0 | (R) |
| 7 | 25 (1-(2-naphthyl)ethyl SH) | 0.75 | 74 | 58 | 82 | 9.7 | (R) |
| 8[g] | | 0.75 | 72 | 45 | 59 | 11.8 | (R) |
| 9[h] | 26 (1-(1-naphthyl)ethyl SH) | 0.75 | 96 | 51 | 90 | 36.6 | (R) |

TABLE 2-continued

Evaluation of substrate scope

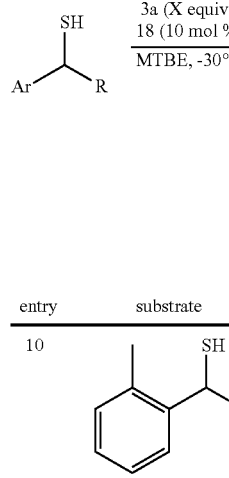

| entry | substrate | X | time (h) | conv. (%)$^a$ | ee$_{thiol}$ (%)$^b$ | S$^c$ | abs. config.$^d$ |
|---|---|---|---|---|---|---|---|
| 10 | 27 | 0.75 | 48 | 50 | 95 (94)$^j$ | 126.0 | (R) |
| 11 | 28 | 0.75 | 48 | 50 | 98 (96)$^j$ | 265.0 | (R) |
| 12$^k$ |  | 0.75 | 48 | 43 | 75 (98)$^j$ | 275.0 | (R) |

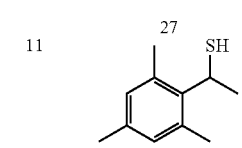

$^a$Refers to conversion, determined using CSP-HPLC, where conversion = 100 × ee$_{thiol}$/(ee$_{thiol}$ + ee$_{thioester}$).
$^b$Determined by CSP-HPLC, see supporting information.
$^c$S = enantioselectivity (k$_{fast}$/k$_{slow}$, see ref. 1).
$^d$Refers to the absolute configuration of the recovered thiol product (see supporting information).
$^e$Data from Table 1.
$^f$A repeat of this experiment (conv. 52%, S = 50.4) resulted in the isolation of the unreacted (R)-thiol in 47% yield and 95% ee after chromatography. After aminolysis of the combined thioester products the (S)-thiol was obtained in 43% isolated yield and 86% ee.
$^g$Reaction at –40° C.
$^h$A repeat of this experiment in which the combined thioester diastereomers were aminolysed resulted in the isolation of the corresponding hemiamide in 93% ee.
$^i$A repeat of this experiment (conv. 51%, S = 249.0) resulted in the isolation of the unreacted (R)-thiol in 48% yield and 99.6% ee after chromatography. After aminolysis of the combined thioester products the (S)-thiol was obtained in 44% isolated yield and 95% ee.
$^j$Value in parenthesis refers to the ee of the thiol obtained after deprotection via cleavage of the combined thioester products.
$^k$Reaction at –45° C.

CONCLUSIONS

Disclosed herein is novel sulfonamide catalyst 18, which promotes the highly enantioselective (S>10) direct acylative KR of a sec-thiols for the first time, allowing their isolation in >90% ee at ca. 50% conversion. Under optimum conditions at low catalyst loadings the selectivity (k$_{fast}$/k$_{slow}$) of these processes is in the range of 50-275, thus using the artificial catalyst 18 it is possible to achieve levels of enantiodiscrimination more usually associated with acylative KR by biological catalysts, using a substrate class not hitherto demonstrated to be generally amenable to enzyme-mediated direct acylative KR. In addition, the thiol-KR is accompanied by a synergistic, simultaneous desymmetrisation of an achiral anhydride electrophile—which occurs with excellent levels of enantioselectivity on a par with those associated with the best anhydride desymmetrisation methodologies in the literature. This catalytic desymmetrisation of an electrophile while it kinetically resolves a nucleophile is, to the best of our knowledge, a hitherto unreported phenomenon which possesses excellent potential as a tool to considerably improve upon both the synthetic utility and atom economy of acylative KR processes.

Experimental General

Proton Nuclear Magnetic Resonance spectra were recorded on a 400 MHz spectrometer in CDCl$_3$ (to prevent oxidation of the thiols, CDCl$_3$ was purified by distillation and stored under argon over molecular sieves) or DMSO-d$_6$ and referenced relative to residual CHCl$_3$ (δ=7.26 ppm) or DMSO (δ=2.54 ppm). Chemical shifts are reported in ppm and coupling constants in Hertz. Carbon NMR spectra were recorded on the same instrument (100 MHz) with total proton decoupling. All melting points are uncorrected. Flash chromatography was carried out using silica gel, particle size 0.04-0.063 mm. TLC analysis was performed on precoated 60F$_{254}$ slides, and visualised by UV irradiation and KMnO$_4$ staining. Optical rotation measurements are quoted in units of 10$^{-1}$ deg cm$^2$ g$^{-1}$. Toluene and methylene chloride were distilled over calcium hydride and stored under argon. Tetrahydrofuran and diethyl ether were distilled over sodium-benzophenone ketyl radical and stored under argon. Commercially available anhydrous t-butyl methyl ether was used. All reactions were carried out under a protective argon atmosphere. Analytical CSP-HPLC was performed on a Daicel CHIRALPAK AS, AD, or Chiralcel OD-H (4.6 mm×25 cm) columns. The absolute configuration of each enantioenriched thiol was determined after derivatisation with (R)-2-methoxy-2-phenylacetic acid and analysis of the corresponding thioester by $^1$H NMR spectroscopy as recently reported in the literature. In the cases of thiols 20 and 25, the absolute configuration (and fidelity of the literature $^1$H NMR spectroscopic method) could be also confirmed by comparison of the optical rotation with the literature data.

Synthesis of Secondary Thiols

All secondary thiols were obtained from the corresponding thioester by reaction with LiAlH$_4$ in anhydrous THF. Thioesters 20, 21, 23, 24 and 27 were made from the corresponding alcohols via a modification of the Mitsunobu protocol. Thioesters 1, 22, 25, 26 and 28 were obtained from the corresponding alcohols via a two step procedure involving initial activation of the hydroxyl function by conversion to the corresponding mesylate (1, 25, 26 and 28) or bromide (22) followed by displacement with the potassium salt of thioacetic acid in acetone or DMF.

General Procedure for the Preparation of Thioesters Via the Mitsunobu Protocol

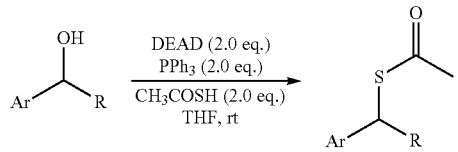

Diisopropyl azodicarboxylate (DEAD) (2.95 mL, 15.0 mmol) was added dropwise and via syringe to an ice-cooled solution of triphenylphosphine (3.93 g, 15.0 mmol) in dry THF (30 mL) under argon. After 1 h, a solution of the appropriate alcohol (7.50 mmol) and thioacetic acid (1.07 mL, 15.0 mmol) in THF (10 mL) was slowly injected and the mixture was stirred continuously while warming to room temperature. After 12 h, the solvent was evaporated in vacuo and the resulting yellow slurry was suspended in n-hexane (40 mL) and stirred for 2 h. After removal of the precipitate that had formed by filtration, the filtrate was concentrated in vacuo and the desired product obtained as colourless oil after purification by flash chromatography on silica gel.

1-Phenylethyl thioacetate

Following the general procedure outlined above, the product was isolated in 75% yield as a colourless oil.

TLC (Hexane:AcOEt, 96:4 v/v): R$_f$=0.40. $^1$H NMR (400 MHz, CDCl$_3$): δ 7.40-7.23 (m, 5H), 4.77 (q, J=7.0 Hz, 1H), 2.33 (s, 3H), 1.68 (d, J=7.0 Hz, 3H). $^{13}$C NMR (100 MHz, CDCl$_3$): δ 194.6 (q), 142.1 (q), 128.1, 126.9, 126.7, 42.5, 30.0, 21.7.

Thioacetic acid S-[1-(4-methoxy-phenyl)-ethyl]ester

Following the general procedure outlined above, the product was isolated in 58% yield as a colourless oil.

TLC (Hexane:CH$_2$Cl$_2$, 7:3 v/v): R$_f$=0.30. $^1$H NMR (400 MHz, CDCl$_3$): δ 7.28 (d, J=8.5 Hz, 2H), 6.87 (d, J=8.5 Hz, 2H), 4.74 (q, J=7.0 Hz, 1H), 3.82 (s, 3H), 2.32 (s, 3H), 1.67 (d, J=7.0 Hz, 3H). $^{13}$C NMR (100 MHz, CDCl$_3$): δ 195.3 (q), 158.7 (q), 134.6 (q), 128.3, 113.9, 55.3, 42.5, 30.5, 22.3. HRMS (m/z): [M+H]$^+$ calcd. for C$_{11}$H$_{15}$O$_2$S 211.0793. found, 211.0797.

Thioacetic acid S-[1-(4-chloro-phenyl)-ethyl]ester

Following the general procedure outlined above, the product was isolated in 90% yield as a colourless oil.

TLC (Hexane:CH$_2$Cl$_2$, 7:3 v/v): R$_f$=0.37. $^1$H NMR (400 MHz, CDCl$_3$): δ 7.30 (m, 4H), 4.73 (q, J=7.3 Hz, 1H), 2.32 (s, 3H), 1.65 (d, J=7.3 Hz, 3H). $^{13}$C NMR (100 MHz, CDCl$_3$): δ 194.4 (q), 140.9 (q), 132.5 (q), 128.2, 128.1, 41.8, 30.0, 21.5. HRMS (m/z): [M+H]$^+$ calcd. for C$_{10}$H$_{12}$OSCl 215.0297. found, 215.0301.

Thioacetic acid S-(1-o-tolyl-ethyl) ester

Following the general procedure outlined above, the product was isolated in 76% yield as a colourless oil.

TLC (Hexane:CH$_2$Cl$_2$, 7:3 v/v): R$_f$=0.34. $^1$H NMR (400 MHz, CDCl$_3$): δ 7.34 (d, J=7.0 Hz, 1H), 7.25-7.15 (m, 3H), 4.95 (q, J=7.0 Hz, 1H), 2.41 (s, 3H), 2.34 (s, 3H), 1.68 (d, J=7.0 Hz, 3H). $^{13}$C NMR (100 MHz, CDCl$_3$): δ 195.0 (q), 139.4 (q), 135.1 (q), 130.1, 126.8, 126.2, 125.8, 38.9, 29.9, 21.6, 18.8. HRMS (m/z): [M+Na]$^+$ calcd. for C$_{11}$H$_{14}$ONaS 217.0663. found, 217.0668.

Thioacetic acid S-(1-phenyl-propyl) ester

Following the general procedure outlined above, the product was isolated in 73% yield as a colourless oil.

TLC (Hexane:CH$_2$Cl$_2$, 1:1 v/v): R$_f$=0.51. $^1$H NMR (400 MHz, CDCl$_3$): δ 7.38-7.23 (m, 5H), 4.51 (t, J=7.5 Hz, 1H), 2.32 (s, 3H), 2.04-1.92 (m, 2H), 0.93 (t, J=7.0 Hz, 3H). $^{13}$C NMR (100 MHz, CDCl$_3$): δ 194.5 (q), 141.3 (q), 128.1, 127.2, 126.8, 49.2, 30.1, 28.9, 11.7. HRMS (m/z): [M+Na]$^+$ calcd. for C$_{11}$H$_{14}$ONaS 217.0663. found, 217.0665.

General Procedure for the Preparation of Thioesters Via the Mesylate Intermediate

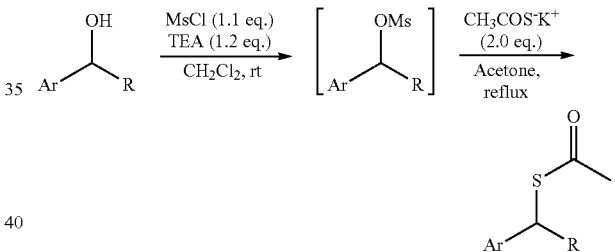

Triethylamine (TEA) (1.25 mL, 9.00 mmol) was added via syringe to a solution of the appropriate alcohol (7.50 mmol) in dry CH$_2$Cl$_2$ (30 mL) under an argon atmosphere. The mixture was cooled to 0° C. and methanesulfonyl chloride (640 μL, 8.25 mmol) was added dropwise. The reaction was stirred continuously while it warmed to room temperature. After 12 h, the mixture was poured into an aqueous solution of HCl (1 N, 30 mL), the resulting mixture was then transferred to a separating funnel and the organic and aqueous layers were separated. The aqueous layer was extracted with CH$_2$Cl$_2$ (2×30 mL) and the combined organic layers were washed with HCl (1 N) (30 mL) and a saturated aqueous solution of NaHCO$_3$ (30 mL). The organic phase was then dried over magnesium sulphate, filtered and evaporated to afford the desired intermediate as a colourless oil. This was immediately dissolved in dry acetone (10 mL) and potassium thioacetate (1.71 g, 15.0 mmol) was added. The reaction was then heated to reflux until none of the mesylate intermediate could be detected by $^1$H-NMR spectroscopic analysis (12-28 h). The mixture was then filtered, the filtrate evaporated and the crude purified by flash-chromatography.

Thioacetic acid (2-methyl-1-phenyl-propyl) ester

Following the general procedure outlined above, the product was isolated in 74% yield as a colourless oil.

TLC (Hexane:CH$_2$Cl$_2$, 7:3 v/v): R$_f$=0.42. NMR (400 MHz, CDCl$_3$): δ 7.22-7.35 (m, 5H), 4.44 (d, J=8.0 Hz, 1H), 2.32 (s, 3H), 2.08-2.22 (m, 1H), 1.06 (d, J=6.5 Hz, 3H), 0.89 (d, J=6.5 Hz, 3H). $^{13}$C NMR (100 MHz, CDCl$_3$): δ 194.2 (q), 141.2 (q), 127.8, 127.7, 126.5, 54.8, 33.1, 30.2, 20.3, 20.1. HRMS (m/z): [M+Na]$^+$ calcd. for C$_{12}$H$_{16}$ONaS 231.0820. found, 231.0819.

Thioacetic acid S-(1-naphthalen-1-yl-ethyl) ester

Following the general procedure, the product was isolated in 69% yield as a colourless oil.

TLC (Hexane:CH$_2$Cl$_2$, 7:3 v/v): R$_f$=0.34. $^1$H NMR (400 MHz, CDCl$_3$): δ 8.09 (d, J=8.5 Hz, 1H), 7.89 (d, J=8.0 Hz, 1H), 7.81 (d, J=8.5 Hz, 1H), 7.61-7.43 (m, 4H), 5.56 (q, J=7.0 Hz, 1H), 2.37 (s, 3H), 1.87 (d, J=7.0 Hz, 3H). $^{13}$C NMR (100 MHz, CDCl$_3$): δ 195.1 (q), 136.8 (q), 133.5 (q), 130.1 (q), 128.5, 127.8, 125.9, 125.4, 124.8, 124.1, 122.7, 38.2, 29.9, 21.8. HRMS (m/z): [M+Na]$^+$ calcd. for C$_{14}$H$_{14}$ONaS 253.0663. found, 253.0659.

Thioacetic acid S-(1-naphthalen-2-yl-ethyl) ester

Following the general procedure outlined above, the product was isolated in 62% yield as a colourless oil.

TLC (Hexane:CH$_2$Cl$_2$, 7:3 v/v): R$_f$=0.31. $^1$H NMR (400 MHz, CDCl$_3$): δ 7.88-7.80 (m, 4H), 7.54-7.44 (m, 3H), 4.95 (q, J=7.0 Hz, 1H), 2.34 (s, 3H), 1.78 (d, J=7.0 Hz, 3H). $^{13}$C NMR (100 MHz, CDCl$_3$): δ 194.6 (q), 139.4 (q), 132.8 (q), 132.2 (q), 128.0, 127.4, 127.1, 125.8, 125.5, 125.2, 125.1, 42.6, 30.0, 21.6. HRMS (m/z): [M+H]$^+$ calcd. for C$_{14}$H$_{15}$ONS 231.0844. found, 231.0848.

Thioacetic acid 1-(2,4,6-trimethyl-phenyl)-ethyl ester

Following the general procedure outlined above, the product was isolated in 62% yield as a colourless oil.

TLC (Hexane:CH$_2$Cl$_2$, 7:3 v/v): R$_f$=0.40. $^1$H NMR (400 MHz, CDCl$_3$): δ 6.85 (s, 2H), 5.35 (q, J=7.5 Hz, 1H), 2.44 (s, 6H), 2.33 (s, 3H), 2.26 (s, 3H), 1.67 (d, J=7.5 Hz, 3H). $^{13}$C NMR (100 MHz, CDCl$_3$): 195.0 (q), 136.3 (q), 136.1 (q), 135.4 (q), 135.2 (q), 130.3, 128.7, 37.4, 29.9, 21.0, 20.7, 20.5, 20.3 Note: this compound exhibits NMR spectra consistent with restricted rotation which is fast on the $^1$H NMR spectroscopic time scale but slow on the $^{13}$C NMR spectroscopic time scale. HRMS (m/z): [M+Na]$^+$ calcd. for C$_{13}$H$_{18}$ONaS 245.0976. found, 245.0974.

Thioacetic acid S-(2,2-dimethyl-1-phenyl-propyl) ester (1-Bromo-2,2-dimethyl-propyl)-benzene (1.00 g, 4.40 mmol) was dissolved in dry DMF (5 mL) under an argon atmosphere. Potassium thioacetate (2.51 g, 22.0 mmol) was added and the reaction was heated to 50° C. for 7 days. The solution was then concentrated and the product purified by column chromatography to obtain the desired thioester (970 mg, 99%). TLC (Hexane:CH$_2$Cl$_2$, 7:3 v/v): R$_f$=0.40. $^1$H NMR (400 MHz, CDCl$_3$): δ 7.33-7.22 (m, 5H), 4.52 (s, 1H), 2.32 (s, 3H), 1.00 (s, 9H). $^{13}$C NMR (100 MHz, CDCl$_3$): δ 193.9 (q), 140.4 (q), 129.0, 127.2, 126.4, 58.7, 34.9 (q), 30.2, 27.6. HRMS (m/z): [M+Na]$^+$ calcd. for C$_{13}$H$_{18}$ONaS 245.0976. found, 245.0972.

General Procedure for the Reduction of Thioesters to Thiols

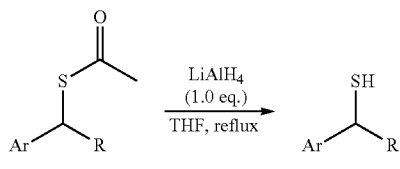

A 100 mL three neck round-bottomed flask, flame dried and equipped with a reflux condenser, was charged with dry THF (15 mL) and LiAlH$_4$ (114 mg, 3.0 mmol). The suspension was cooled to 0° C. and a solution of the appropriate thioester (3.0 mmol) in dry THF (5 mL) was added in a dropwise manner. After 1 h refluxing, the reaction mixture was cooled to 0° C. and carefully quenched with aqueous HCl (1 M) (10 mL). The organic layer was separated and the aqueous solution extracted with Et$_2$O (2×15 mL). The combined organic layers were then dried over magnesium sulphate, filtered and evaporated and the desired product obtained in excellent yield after purification by flash-chromatography on silica gel.

Synthesis of catalyst 18—2,4,6-Triisopropyl-N-[(6-methoxy-quinolinyl)-(5-vinyl-1-azabicyclo[2.2.2.]octyl)-methyl]benzenesulfonamide

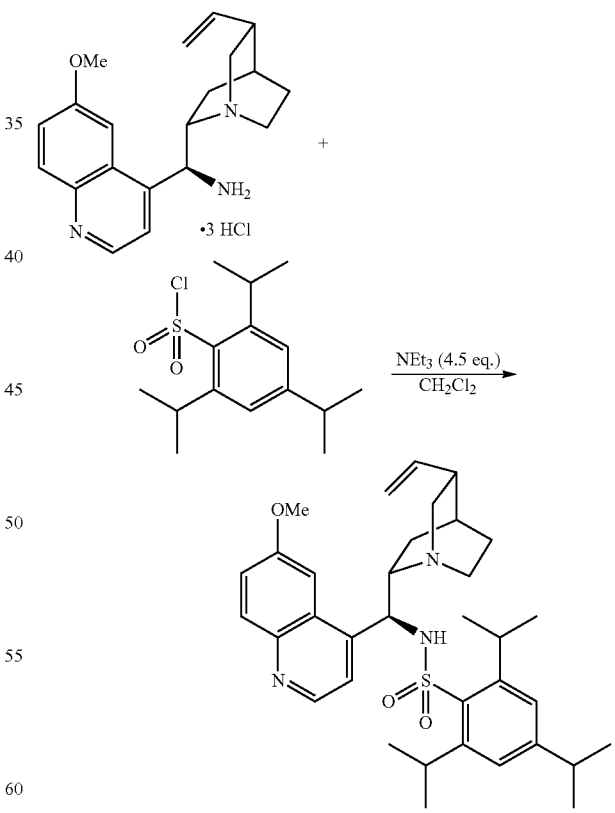

To a suspension of 9-epi-QA.3HCl (1.0 g, 2.31 mmol) in dry CH$_2$Cl$_2$ (20 mL), triethylamine (1.5 mL, 10.4 mmol) was then added via syringe and the resulting clear solution was cooled to 0° C. A solution of 2,4,6-Triisopropyl-phenyl sulphonyl chloride (700 mg, 2.31 mmol) in CH$_2$Cl$_2$ (5 mL) was then slowly injected and the mixture was allowed to warm to room temperature and stirred for 15 h. After evaporation of the solvent, the crude residue was purified by flash chromatography affording the desired sulphonamide catalyst 18 (1.10 g, 81%). M.p. 115-118° C.; TLC (Hexane:EtOAc, 1:1 v/v): $R_f$=0.48. $[\alpha]^{20}_{589}$=−43.0 (c=0.50, CHCl$_3$). $^1$H NMR (400 MHz, DMSO-d$_6$ only the major rotamer quoted): δ 8.52 (d, 1H, J=4.4 Hz), 7.92 (d, 1H, J=9.7 Hz), 7.47-7.41 (m, 2H), 7.40 (d, 1H, J=4.4 Hz), 6.99 (s, 2H), 5.73-5.70 (m, 1H), 5.16 (d, 1H, J=10.4 Hz), 4.96 (d, 1H, J=17.3 Hz), 4.89 (d, 1H, J=10.6 Hz), 3.96 (s, 3H, OCH$_3$), 3.83-3.94 (m, 3H), 3.07-3.09 (m, 1H), 2.81-2.93 (m, 3H), 2.63-2.68 (m, 1H), 2.46-2.48 (m, 1H), 2.21 (bs, 1H), 1.42-1.58 (m, 3H), 1.13-1.16 (m, 12H), 0.87 (d, 6H, J=6.5 Hz), 0.71-0.78 (m, 1H). $^{13}$C NMR (100 MHz, DMSO-d$_6$): δ 157.7, 152.1, 149.2, 147.8, 144.8, 144.1, 142.2, 134.6, 131.9, 127.9, 123.3, 121.2, 120.8, 114.7, 102.2, 60.7, 56.0, 55.3, 52.3, 40.3, 39.3, 33.7, 29.6, 27.8, 27.4, 25.4, 25.2, 24.6, 23.8. IR (neat): 3658, 2981, 2889, 1473, 1462, 1382, 1252, 1150, 1072, 954 cm$^{-1}$. HRMS (m/z): [M+H]$^+$ calcd. for C$_{35}$H$_{48}$N$_3$O$_3$S 590.3416. found, 590.3410.

Catalyst Evaluation at Low Temperature (General Procedure A)

A 20 mL reaction vial containing a stirring bar was charged with 3-methylglutaric anhydride (3a) (28.8 mg, 0.225 mmol) and 18 (17.7 mg, 0.030 mmol). The reaction vial was flushed with argon and fitted with a septum. MTBE (degassed) was then injected (1.5 mL, 0.2M) and the solution cooled to −30° C. The relevant thiol (0.30 mmol) was added via syringe and the resulting solution was stirred for the time indicated in Table 2. Conversion to the product was then monitored by $^1$H-NMR spectroscopic analysis and the mixture was purified by flash-chromatography in order to separate the unreacted thiol from the thioester product.

Enantiomeric Excess, Conversion and S Factor Determination Procedures (Table 2)

The enantiomeric excess of each unreacted thiol was determined by CSP-HPLC after conversion to the corresponding Michael adduct with acrylonitrile. The enantiomeric excess of each 'fast reacting' thiol was determined by CSP-HPLC after aminolysis of the thioester product and derivatisation of the thiol to the corresponding Michael adduct with acrylonitrile. Conversion was determined using CSP-HPLC, where conversion=100×ee$_{thiol}$/(ee$_{thiol}$+ee$_{thioester}$) and the Selectivity Factor (S) was calculated according to the method developed by Kagan (Kagan, H. B. & Fiaud, J. C. Kinetic resolution. *Top. Stereochem.* 18, 249-330 (1988)).

Thiol Derivatisation (General Procedure B)

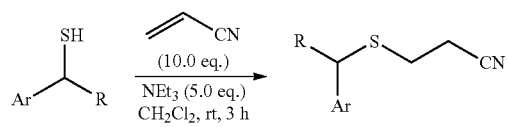

The appropriate 'slow reacting' thiol (as obtained after flash-chromatography of the crude reaction mixture) was dissolved in CH$_2$Cl$_2$ (1.0 mL) under an argon atmosphere. Triethylamine (5.0 eq.) and acrylonitrile (10.0 eq.) were added and the mixture was stirred at room temperature for 3 h. After removal of the volatiles under reduced pressure, the crude product was then purified by flash-chromatography to afford the desired Michael adduct in quantitative yield.

One-Pot Thioester Aminolysis and Thiol Derivatisation (General Procedure C)

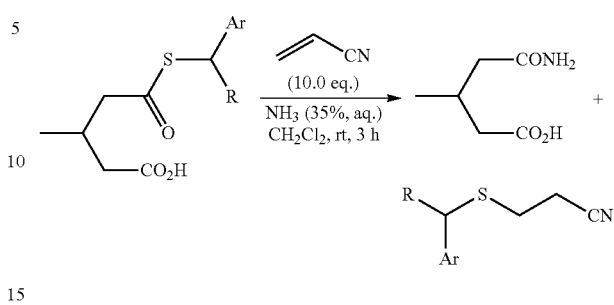

The appropriate thioester (as obtained after flash-chromatography of the reaction crude) was dissolved in CH$_2$Cl$_2$ (3.0 mL). Acrylonitrile (10.0 eq.) and ammonia (35% aqueous solution, 3.0 mL) were added and the biphasic mixture was vigorously stirred at room temperature for 3 h. The reaction was then diluted with CH$_2$Cl$_2$ (10.0 mL) and H$_2$O (10.0 mL) and transferred to a separating funnel. The organic and aqueous layers were separated and the organic layer was dried over MgSO$_4$, filtered and evaporated under reducer pressure. The desired Michael addition product was obtained in quantitative yield after purification by flash-chromatography.

Thioester Derivatisation as the Corresponding o-Nitrophenyl Ester (Table 1)

Enantioselectivity data in Table 2 were obtained by recovering the unreacted thiol and separating it from the thioester products, which were then aminolysed to the other thiol antipode and analysed separately by CSP-HPLC. In Table 1 however, enantioselectivity data were available from analysis of the thioester diastereomers, which were readily separable by CSP-HPLC after conversion to the corresponding o-nitrophenylester derivatives via the procedure outlined below.

A 5 mL reaction vial containing a stirring bar was charged with the thioester (as obtained after flash-chromatography of the reaction crude), o-nitrophenol (2.0 eq.), DMAP (0.1 eq.), DCC (1.2 eq.) and CH$_2$Cl$_2$ (0.05 M). The reaction vial was flushed with argon, fitted with a septum and stirred at room temperature for 12 h. The mixture was then filtered and the resulting clear solution was then purified by flash-chromatography.

Characterisation Data

Where indicated the absolute configuration of the thiols was established by following the literature procedure of Porto, S., Seco, J. M., Ortiz, A., Quiñoá, E. & Riguera, R. Chiral thiols: the assignment of their absolute configuration by $^1$H NMR. *Org. Lett.* 24, 5015-5018 (2007).

3-Methyl-4-(2-methyl-1-phenyl-propylsulfanylcarbonyl)-butyric acid (Table 1, entry 19)

TLC (n-Hexane:EtOAc, 97:3, v/v): $R_f$=0.38. $^1$H NMR (400 MHz, CDCl$_3$): δ 7.31-7.20 (m, 5H), 4.43 (d, J=8.0 Hz, 1H), 2.66-2.36 (m, 4H), 2.26-2.20 (m, 1H), 2.18-2.06 (m, 1H), 1.02 (d, J=7.0 Hz, 3H), 0.98 (d, J=6.5 Hz, 3H), 0.86 (d, J=6.5 Hz, 3H). $^{13}$C NMR (100 MHz, CDCl$_3$): δ 197.0, 176.6, 141.5, 128.3, 128.2, 127.0, 55.2, 50.0, 40.0, 33.6, 27.9, 20.7, 20.5, 19.5; IR (neat): 2965, 2931, 1704, 1685, 1450, 1007, 911, 727, 697 cm$^{-1}$. HRMS (m/z): [M+Na]$^+$ calcd. for C$_{16}$H$_{22}$O$_3$NaS 317.1187. found, 317.1198. Note: Major diastereomer is 7a

2-Methyl-1-phenyl-propane-1-thiol ((R)-1, table 1, entry 19)

After 68 h, the enantioenriched unreacted thiol was recovered in 90.4% ee as determined by CSP-HPLC after conversion to the corresponding Michael addition adduct following the general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 12.3 min (minor enantiomer) and 14.0 min (major enantiomer).

Conversion=53.5%; S Factor=25.5.

TLC (Hexane:CH$_2$Cl$_2$, 9:1 v/v): R$_f$=0.52. [α]$^{20}_D$=+99.0 (c=0.54, CHCl$_3$). $^1$H NMR (400 MHz, CDCl$_3$): δ 7.36-7.20 (m, 5H), 3.78 (dd, J=8.5 and 5.0 Hz, 1H), 2.20-2.05 (m, 1H), 1.83 (d, J=5.0 Hz, 1H), 1.12 (d, J=6.5 Hz, 3H), 0.85 (d, J=6.5 Hz, 3H). $^{13}$C NMR (100 MHz, CDCl$_3$): δ 143.8 (q), 127.9, 127.0, 126.5, 51.5, 35.4, 20.4, 20.3. HRMS (m/z): [M]$^+$ calcd. for C$_{10}$H$_{14}$S 166.0816. found, 166.0810.

The absolute configuration of 1 was established following the literature procedure.

1-Phenylethanethiol ((R)-20, Table 2, entry 1)

After 68 h, the enantioenriched unreacted (R)-thiol was recovered in 97.1% ee as determined by CSP-HPLC after conversion to the corresponding Michael addition adduct following general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 14.6 min (minor enantiomer) and 16.1 min (major enantiomer).

TLC (Hexane:CH$_2$Cl$_2$, 9:1 v/v): R$_f$=0.49. [α]$^{20}_D$=+62.0 (c=0.38, EtOH); Lit. [α]$^{25}_D$=−88.7 (c=0.63, EtOH; 99% ee, (S)-enantiomer)$^3$. $^1$H NMR (400 MHz, CDCl$_3$): δ 7.42-7.23 (m, 5H), 4.26 (app quintet, J=6.5 Hz, 1H), 2.02 (d, J=5.0 Hz, 1H), 1.70 (d, J=7.0 Hz, 3H). $^{13}$C NMR (100 MHz, CDCl$_3$): δ 145.4 (q), 128.2, 126.7, 125.9, 38.3, 25.6. HRMS (m/z): [M+H]$^+$ calcd. for C$_8$H$_{11}$S 139.058. found, 139.0585.

After aminolysis of the thioester product and derivatisation as per general procedure C, the reacted enantioenriched thiol was recovered in 57.4% ee. Conversion=62.8%; S Factor=14.5.

The absolute configuration of 20 was established following the procedure reported in the literature and (with agreement) by comparing the optical rotation with the literature data.

1-Phenyl-propane-1-thiol ((R)-21, Table 2, entry 2)

After 74 h, the enantioenriched unreacted (R)-thiol was recovered in 91.2% ee as determined by CSP-HPLC after conversion to the corresponding Michael addition adduct following the general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 11.4 min (minor enantiomer) and 13.2 min (major enantiomer).

TLC (Hexane:CH$_2$Cl$_2$, 9:1 v/v): R$_f$=0.45. [α]$^{20}_D$=+70.2 (c=0.45, CHCl$_3$). $^1$H NMR (400 MHz, CDCl$_3$): δ 7.38-7.22 (m, 5H), 3.92 (dt, J=7.5 and 5.0 Hz, 1H), 2.07-1.90 (m, 3H), 0.96 (t, J=7.5 Hz, 3H). $^{13}$C NMR (100 MHz, CDCl$_3$): δ 144.1 (q), 128.1, 126.7, 126.5, 45.5, 32.4, 12.1. HRMS (m/z): [M]$^+$ calcd. for C$_9$H$_{12}$S 152.0660. found, 152.0653.

After aminolysis of the thioester product and derivatisation as per general procedure C, the reacted enantioenriched thiol was recovered in 72.0% ee. Conversion=55.9%; S Factor=19.0.

The absolute configuration of 21 was established following the procedure reported in the literature.

2,2-Dimethyl-1-phenyl-propane-1-thiol ((R)-22, Table 2, entry 4)

After 96 h, the enantioenriched unreacted (R)-thiol was recovered in 93.8% ee as determined by CSP-HPLC after conversion to the corresponding Michael addition adduct following the general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 9.5 min (major enantiomer) and 11.7 min (minor enantiomer).

TLC (Hexane 100%): R$_f$=0.36. [α]$^{20}_D$=+105.4 (c=0.51, CHCl$_3$). $^1$H NMR (400 MHz, CDCl$_3$): δ 7.38-7.20 (m, 5H). 3.99 (d, J=5.0 Hz, 1H), 1.77 (d, J=5.0 Hz, 1H), 1.03 (s, 9H). $^{13}$C NMR (100 MHz, CDCl$_3$): δ 142.3 (q), 128.4, 127.2, 126.5, 55.4 (q), 35.1, 27.2. HRMS (m/z): [M]$^+$ calcd. for C$_{11}$H$_{16}$S 180.0973. found, 180.0975.

After hydrolysis of the thioester product and derivatisation as per general procedure C, the reacted enantioenriched thiol was recovered in 87.2% ee. Conversion=51.8%; S Factor=51.5. The absolute configuration of 22 was established following the procedure reported in the literature. A repeat of this experiment (cony. 52%, S=50.4) resulted in the isolation of the unreacted (R)-thiol in 47% yield and 94.8% ee. After aminolysis of the combined thioester products the (S)-thiol was obtained in 43% isolated yield and 86.26% ee.

1-(4-Chloro-phenyl)-ethanethiol ((R)-23, Table 2, entry 5)

After 72 h, the enantioenriched unreacted (R)-thiol was recovered in 95.3% ee as determined by CSP-HPLC after conversion to the corresponding Michael addition adduct following the general procedure B.

CSP-HPLC analysis. Chiralpak AS (4.6 mm×25 cm), hexane/IPA: 96/4, 1.0 mL min$^{-1}$, RT, UV detection at 220 nm, retention times: 17.1 min (major enantiomer) and 18.7 min (minor enantiomer).

TLC (Hexane:CH$_2$Cl$_2$, 9:1 v/v): R$_f$=0.52. [α]$^{20}_D$=+73.7 (c=0.36, CHCl$_3$). $^1$H NMR (400 MHz, CDCl$_3$): δ 7.32 (br s, 4H), 4.23 (dq, J=7.0 and 5.0 Hz, 1H), 2.01 (d, J=5.0 Hz), 1.67 (d, J=7.0 Hz, 3H); $^{13}$C NMR (100 MHz, CDCl$_3$): δ 143.9 (q), 132.3 (q), 128.4, 127.3, 37.6, 25.5. HRMS (m/z): [M+H]$^+$ calcd. for C$_8$H$_{10}$SCl 173.0192. found, 173.0191.

After aminolysis of the thioester product and derivatisation as per general procedure C, the reacted enantioenriched thiol was recovered in 51.0% ee. Conversion=65.1%; S Factor=10.7. The absolute configuration of 23 was established following the procedure reported in the literature.

1-(4-Methoxy-phenyl)-ethanethiol ((R)-24, Table 2, entry 6)

After 5 d, the enantioenriched unreacted (R)-thiol was recovered in 87.1% ee as determined by CSP-HPLC after conversion to the corresponding Michael addition adduct following the general procedure B.

CSP-HPLC analysis. Chiralpak OD-H (4.6 mm×25 cm), hexane/IPA: 98/2, 1.0 mL min$^{-1}$, RT, UV detection at 220 nm, retention times: 22.3 min (minor enantiomer) and 24.1 min (major enantiomer).

TLC (Hexane:CH$_2$Cl$_2$, 8:2, v/v): R$_f$=0.35. [α]$^{20}_D$=+47.3 (c=0.30, CHCl$_3$). $^1$H NMR (400 MHz, CDCl$_3$): δ 7.32 (d, J=8.5 Hz, 2H), 6.88 (d, J=8.5 Hz, 2H), 4.25 (dq, J=7.0 and 5.0

Hz, 1H), 3.82 (s, 3H), 2.00 (d, J=5.0 Hz), 1.67 (d, J=7.0 Hz, 3H). $^{13}$C NMR (100 MHz, CDCl$_3$): δ 158.6 (q), 137.9 (q), 127.4, 113.9, 55.3, 38.2, 26.3. HRMS (m/z): [M+H]$^+$ calcd. for C$_9$H$_{13}$OS 169.0687. found, 169.0683.

After aminolysis of the thioester product and derivatisation as per general procedure C, the reacted enantioenriched thiol was recovered in 68.8% ee. Conversion=55.8%; S Factor=15.0. The absolute configuration of 24 was established following the procedure reported in the literature.

1-Naphthalen-2-yl-ethanethiol ((R)-25, Table 2, entry 7)

After 74 h, the enantioenriched unreacted thiol was recovered in 82.0% ee as determined by CSP-HPLC after conversion to the corresponding Michael addition adduct following the general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 18.2 min (minor enantiomer) and 23.7 min (major enantiomer).

TLC (Hexane:CH$_2$Cl$_2$, 9:1 v/v): R$_f$=0.47. [α]$^{20}$$_D$=+53.7 (c=0.38, CH$_2$Cl$_2$); Lit [α]$^{20}$$_D$=+65.9 (c=0.58, CH$_2$Cl$_2$; 99% ee, (R)-enantiomer). $^1$H NMR (400 MHz, CDCl$_3$): δ 7.89-7.82 (m, 3H), 7.91-7.78 (m, 1H), 7.58 (dd, J=8.5 and 1.8 Hz, 1H), 7.54-7.47 (m, 2H), 4.44 (dq, J=7.0 and 5.0 Hz, 1H), 2.08 (d, J=5.0 Hz, 1H), 1.80 (d, J=7.0 Hz, 3H). $^{13}$C NMR (100 MHz, CDCl$_3$): δ 143.2 (q), 133.3 (q), 132.6 (q), 128.5, 127.8, 127.7, 126.2, 125.9, 125.0, 124.4, 39.0, 25.9. HRMS (m/z): [M+H]$^+$ calcd. for C$_{12}$H$_{13}$S 189.0738. found, 189.0736.

After aminolysis of the thioester product and derivatisation as per general procedure C, the reacted enantioenriched thiol was recovered in 59.5% ee. Conversion=57.9%; S Factor=9.7. The absolute configuration of 25 was established following the procedure reported in the literature and (with agreement) by comparing the optical rotation with the literature data.

1-Naphthalen-1-yl-ethanethiol ((R)-26, Table 2, entry 8)

After 96 h, the enantioenriched unreacted (R)-thiol was recovered in 89.8% ee as determined by CSP-HPLC after conversion to the corresponding Michael addition adduct following the general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 22.4 min (minor enantiomer) and 28.1 min (major enantiomer).

TLC (Hexane:CH$_2$Cl$_2$, 9:1 v/v): R$_f$=0.39. [α]$^{20}$$_D$=-188.0 (c=0.40, CHCl$_3$). $^1$H NMR (400 MHz, CDCl$_3$): δ 8.19 (d, J=8.5 Hz, 1H), 7.90 (d, J=8.0 Hz, 1H), 7.79 (d, J=8.0 Hz, 1H), 7.69 (d, J=7.0 Hz, 1H), 7.60 (t, J=7.0 Hz, 1H), 7.56-7.46 (m, 2H), 5.12-5.02 (m, 1H), 2.16 (d, J=5.0 Hz, 1H), 1.90 (d, J=7.0 Hz, 3H). $^{13}$C NMR (100 MHz, CDCl$_3$): δ 140.6 (q), 133.5 (q), 129.9 (q), 128.6, 127.3, 125.8, 125.2, 125.1, 122.5, 122.2, 33.2, 24.7. HRMS (m/z): [M+H]$^+$ calcd. for C$_{12}$H$_{13}$S 189.0738. found, 189.0736.

After aminolysis of the thioester product and derivatisation as per general procedure C, the reacted enantioenriched thiol was recovered in 84.7% ee. Conversion=51.5; S Factor=36.6. The absolute configuration of 26 was established following the procedure reported in the literature.

In a repeat of this experiment the combined hemithioester products (70.0 mg, 0.22 mmol) were dissolved in CH$_2$Cl$_2$ (2 mL) and treated with aq. NH$_3$ (2 mL). After stirring at room temperature for 4 h, the reaction was then diluted with CH$_2$Cl$_2$ (10.0 mL) and H$_2$O (5.0 mL) and transferred to a separating funnel. The organic and aqueous layers were separated and the aqueous layer was washed with CH$_2$Cl$_2$ (2×10.0 mL). The aqueous layer was then acidified by addition of HCl (2 N) until pH=2.8 and evaporated under reduced pressure. After dissolving the mixture of product and salts in the minimum amount of H$_2$O, the product was extracted with EtOAc (7×10 mL). The combined organic phases were then dried over magnesium sulphate and the solvent was removed under reduced pressure to afford the desired hemiamide as a white solid in 82% yield. (26.0 mg, 0.18 mmol). 93.0% ee as determined by CSP-HPLC after transformation to the corresponding o-nitrophenoxy ester, as per the procedure reported below.

$^1$H NMR (400 MHz, DMSO-d$_6$): δ 7.29 (s, 1H), 6.77 (s, 1H), 2.31-2.15 (m, 2H), 2.11-1.88 (m, 3H), 0.88 (d, J=6.3 Hz, 3H). $^{13}$C NMR (100 MHz, DMSO-d$_6$): δ 173.7 (q), 173.2 (q), 41.8, 40.6, 27.2, 19.4. HRMS (m/z): [M+Na]$^+$ calcd. for C$_6$H$_{11}$NO$_3$Na 168.0637. found, 168.0643.

The enantiomeric excess of the hemiamide was determined by CSP-HPLC after conversion to the corresponding o-nitrophenyl ester.

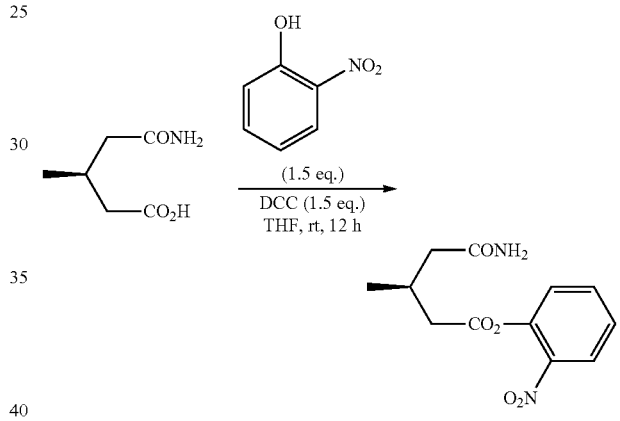

A 5 mL reaction vial containing a stirring bar was charged with the hemiamide (20 mg, 0.137 mmol) and DCC (42.6 mg, 0.206 mmol). 2-nitrophenol (27.8 mg, 0.20 mmol). The vial was flushed with argon and dry THF (0.5 mL) was added. After 10 min, a solution of 2-nitrophenol (28.6 mg, 0.206 mmol) in dry THF (0.5 mL) was then added via syringe and the reaction mixture was stirred for 12 h at room temperature. After filtration of the resulting white precipitate, the filtrate was concentrated in vacuo and the residue purified by chromatography on silica gel to afford the desired compound in 30% yield (11.0 mg). 93.0% ee as determined by CSP-HPLC analysis (chromatogram below). Chiralpak OD-H (4.6 mm×25 cm), hexane/IPA: 90/10, 1.0 mL min$^{-1}$, RT, UV detection at 220 nm, retention times: 48.2 min (minor enantiomer) and 56.5 (major enantiomer).

1-o-Tolyl-ethanethiol ((R)-27, Table 2, entry 9)

After 48 h, the enantioenriched unreacted (R)-thiol was recovered in 95.3% ee as determined by CSP-HPLC after conversion to the corresponding Michael addition adduct following the general procedure B.

CSP-HPLC analysis. Chiralpak OD-H (4.6 mm×25 cm), hexane/IPA: 95/5, 1.0 mL min$^{-1}$, RT, UV detection at 220 nm, retention times: 11.4 min (minor enantiomer) and 13.7 min (major enantiomer).

TLC (Hexane 100%): $R_f$=0.37. $[\alpha]^{20}_{589}$=−17.4 (c=0.42, CHCl$_3$). $^1$H NMR (400 MHz, CDCl$_3$): δ 7.50 (d, J=7.5 Hz, 1H), 7.28-7.21 (m, 1H), 7.20-7.13 (m, 2H), 4.44 (dq, J=7.0 and 6.0 Hz, 1H), 2.43 (s, 3H), 1.93 (d, J=6.0 Hz, 1H), 1.72 (d, J=7.0 Hz, 3H). $^{13}$C NMR (100 MHz, CDCl$_3$): δ 143.0 (q), 134.2 (q), 130.0, 126.4, 126.1, 124.7, 33.8, 25.0, 18.8. HRMS (m/z): [M]$^+$ calcd. for C$_9$H$_{12}$S 152.0660. found, 152.0661.

After aminolysis of the thioester product and derivatisation as per general procedure C, the reacted enantioenriched thiol was recovered in 94.2% ee. Conversion=50.3%; S Factor=126.0.

The absolute configuration of 27 was established following the procedure reported in the literature.

1-(2,4,6-Trimethyl-phenyl)-ethanethiol ((R)-28, Table 2, entry 10)

After 48 h, the enantioenriched unreacted (R)-thiol was recovered in 98.1% ee as determined by CSP-HPLC after conversion to the corresponding Michael addition adduct following the general procedure B.

CSP-HPLC analysis. Chiralpak AS (4.6 mm×25 cm), hexane/IPA: 95/5, 1.0 mL min$^{-1}$, RT, UV detection at 220 nm, retention times: 6.9 min (major enantiomer) and 8.2 min (minor enantiomer).

TLC (Hexane:CH$_2$Cl$_2$, 9:1 v/v): $R_f$=0.44. $[\alpha]^{20}_{589}$=+102.6 (c=0.35, CHCl$_3$). $^1$H NMR (400 MHz, CDCl$_3$): δ 6.84 (s, 2H). 4.81 (dq, J=7.5 and 5.5 Hz, 1H), 2.57 (br s, 3H), 2.38 (br s, 3H), 2.26 (s, 3H) 2.20 (d, J=5.5 Hz, 1H), 1.73 (d, J=7.5 Hz, 3H). $^{13}$C NMR (100 MHz, CDCl$_3$): δ 137.3, 136.4 (q), 135.8, 134.3 (q), 131.0 (q), 128.7 (q), 32.8, 23.1, 20.6, 20.2. HRMS (m/z): [M]$^+$ calcd. for C$_{11}$H$_{16}$S 180.0973. found, 180.0978.

After hydrolysis of the thioester product and derivatisation as per general procedure C, the reacted enantioenriched thiol was recovered in 96.4% ee. Conversion=50.4%; S Factor=265.0.

The absolute configuration of 28 was established following the procedure reported in the literature.

A repeat of this experiment (cony. 51%, S=249) resulted in the isolation of the unreacted (R)-thiol in 48% yield and 99.6% ee. After aminolysis of the combined thioester products the (S)-thiol was obtained in 44% isolated yield and 94.7% ee.

A repeat of this experiment at −45° C. resulted in the isolation of the (R)-thiol in 75.4% ee as determined by CSP-HPLC after conversion to the corresponding Michael addition adduct following the general procedure B.

After hydrolysis of the thioester product and derivatisation as per general procedure C, the reacted enantioenriched thiol was recovered in 98.3% ee. Conversion=43.4%; S Factor=275.0.

HPLC Calculation Methods

3-Methyl-4-(2-methyl-1-phenyl-propylsulfanylcarbonyl)-butyric acid

Chiralpak OD-H (4.6 mm×25 cm), hexane/IPA: 95/5, 1.0 mL min$^{-1}$, RT, UV detection at 220 nm

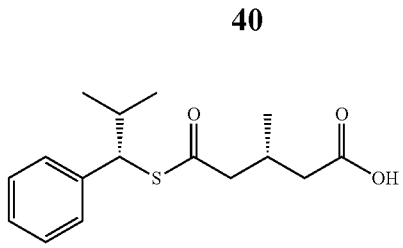

7a

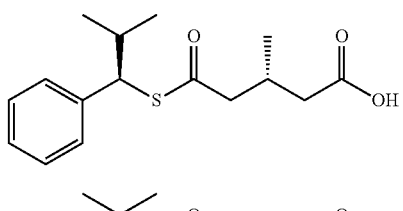

7b

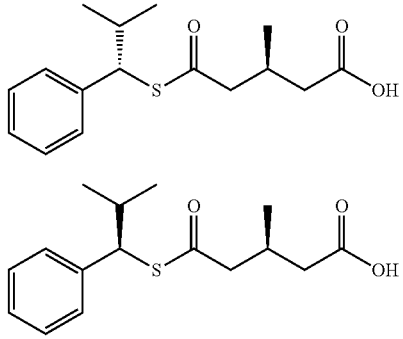

(ent)-7b (ent)-7a

Chromatogram of the thioesters 7a-b (derivatised as their o-nitrophenyl esters for analysis via CSP-HPLC) from the reaction of 1 with 3 in the presence of triethylamine and an achiral thiourea as catalysts. The chromatogram clearly identifies the enantiomeric relationship between the peaks at 16.2 and 23.1 min (7a and its enantiomer) and between those at 17.9 min and 48.0 min (7b and its enantiomer).

| Peak No | Result | Ret. Time (min) |
|---|---|---|
| 1 | 19.870 | 16.199 |
| 2 | 8.148 | 17.894 |
| 3 | 19.780 | 23.066 |
| 4 | 7.983 | 48.045 |

Chromatogram of the thioesters 7a-b (derivatised as their o-nitrophenyl esters for analysis via CSP-HPLC) from the reaction of (S)-1 (84.5% ee) with 3 in the presence of triethylamine and an achiral thiourea as catalysts. The chromatogram clearly allows the identification of the major diastereomer 7a derived from attack of the enantioenriched thiol on a single prochiral carbonyl group to give (R)-stereochemistry at the carbon chain. This is the sense of stereoinduction expected from previous work and confirmed by conversion of a mixture of thioester diastereomers derived from the addition of 22 to 3 catalysed by 18 to a lactone of known configuration (see below). The 84.5% ee relationship between the peaks at 17 and 48 min confirms the identity of ent-7a. Likewise, the larger of the two peaks associated with the 7b diastereomer must therefore be ent-7b (i.e. with (S)-stereochemistry at the carbon bound to the sulphur atom).

| Peak No | Result | Ret. Time (min) |
|---|---|---|
| 1 | 19.603 | 14.618 |
| 2 | 13.613 | 16.034 |

| Peak No | Result | Ret. Time (min) |
|---|---|---|
| 3 | 2.375 | 20.309 |
| 4 | 0.846 | 42.152 |

Determination of the Sense of Stereoinduction Associated with the Desymmetrisation Reaction The sense of stereoinduction associated with the desymmetrisation reaction was determined by conversion of the mixture of thioester diastereomers derived from the addition of 22 to 3 (i.e. Table 2, entry 4) to the lactone shown below and comparison of the optical rotation of that lactone derivative with the literature data (Irwin, A. J. & Jones, J. B. Asymmetric syntheses via enantiotopically selective horse liver alcohol dehydrogenase catalyzed oxidations of diols containing a prochiral center. J. Am. Chem. Soc. 99, 556-561 (1977)).

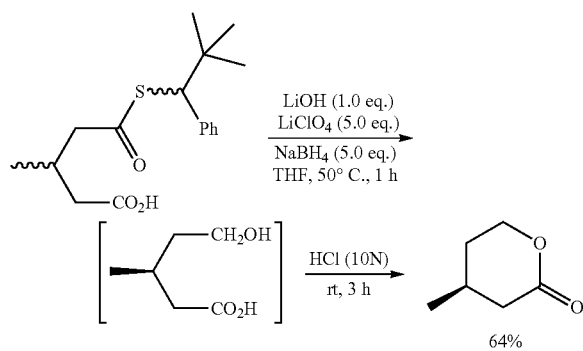

The mixture of thioester diastereomers (92.5 mg, 0.30 mmol) was dissolved in THF (5 mL) and LiOH (12.6 mg, 0.30 mmol) was added. The reaction was heated to 50° C. and stirred for 15 minutes. LiClO$_4$ (159.6 mg, 1.50 mmol) and NaBH$_4$ (56.7 mg, 1.50 mmol) were then added and the reaction mixture was stirred at 50° C. for 1 h. The solvent was concentrated in vacuo, HCl (10 N, 5 mL) was added and the mixture was stirred at room temperature for 3 h. The desired product was extracted with CHCl$_3$ (3×10 mL), the combined extracts were dried (MgSO$_4$), concentrated in vacuo and purified by flash-chromatography to give the lactone shown above as a colourless oil (22.0 mg, 0.19 mmol, 64% yield). $[\alpha]^{20}_D$=−16.5 (c 0.22, CHCl$_3$), Lit. $[\alpha]^{27}_D$=−24.8 (c=1.02, CHCl$_3$; 90% ee, (S)-enantiomer). $^1$H NMR (400 MHz, CDCl$_3$): δ 4.49-4.41 (m, 1H), 4.28 (td, J=10.5 and 3.5 Hz, 1H), 2.76-2.65 (m, 1H), 2.18-2.08 (m, 2H), 2.00-1.90 (m, 1H), 1.61-1.49 (m, 1H), 1.09 (d, J=6.0 Hz, 3H). $^{13}$C NMR (100 MHz, CDCl$_3$): δ 171.0 (q), 68.4, 38.1, 30.5, 26.4, 21.3.

By obtaining the (−) enantiomer of the lactone it is certain (from a comparison with the literature value for the (S) enantiomer of the lactone [Irwin, A. J. & Jones, J. B. Asymmetric syntheses via enantiotopically selective horse liver alcohol dehydrogenase catalyzed oxidations of diols containing a prochiral center. J. Am. Chem. Soc. 99, 556-561 (1977).]) that the major diastereomer derived from the addition of 22 to 3 possessed (R)-stereochemistry at the new stereocenter (which was the 3-position of the glutaric anhydride).

Chromatogram of the thioesters 7a-b (derivatised as their o-nitrophenyl esters for analysis via CSP-HPLC) from the reaction of 1 with 3 in the presence of catalyst 18 under the conditions outlined in Table 1 entry 19. The chromatogram clearly identifies (7a+ent-7a) as the major diastereomer (89:11 dr) and allows the calculation of ee$_{esterA}$, ee$_{esterB}$, ee$_{desymm}$, C and S.

| Peak No | Result | Ret. Time (min) |
|---|---|---|
| 1 | 0.441 | 13.880 |
| 2 | 44.742 | 15.063 |
| 3 | 5.069 | 18.735 |
| 4 | 0.392 | 38.049 |

Calculations:

$dr$=(7a+ent-7a):(7b+ent-7b)

ee$_{esterA}$=100×[(7a−ent-7a)/(7a+ent-7a)]

ee$_{esterB}$=100×[(7b−ent-7b)/(7b+ent-7b)]

ee$_{desymm}$=100×[(7a+7b)−(ent-7a+ent-7b)]/[(7a+7b)+(ent-7a+ent-7b)]

ee$_{thioester}$=100×[(7a+ent-7b)−(7b+ent-7a)]/[(7a+ent-7b)+(7b+ent-7a)]

ee$_{thiol}$=determined by CPS-HPLC analysis, see chromatogram below.

$C$=100×ee$_{thiol}$/(ee$_{thiol}$+ee$_{thioester}$)

Note: C calculated this way correlated precisely (within experimental error) with the conversion levels measured by $^1$H NMR spectroscopy in all cases.

$S$=ln [(1−C)(1−ee$_{thiol}$)]/ln [(1−C)(1−ee$_{thiol}$)] or ln [1−C(1+ee$_{thioester}$)]/ln [1−C(1−ee$_{thioester}$)]

KR of Thiol 28 with Simultaneous Enantioselective Synthesis of a (R)-Pregabalin Precursor A 20 mL reaction vial containing a stirring bar was charged with 3-isobutylglutaric anhydride (4) (102.1 mg, 0.60 mmol) and 18 (47.2 mg, 0.080 mmol). The reaction vial was flushed with argon and fitted with a septum. MTBE was then injected (4.0 mL, 0.2M) and the solution cooled to −30° C. 28 (0.30 mmol) was added dropwise via syringe and the resulting solution was stirred for 48 h. The mixture was the immediately loaded onto a column and the 'slow reacting' thiol enantiomer separated from the mixture by flash-chromatography (71.0 mg, 0.39 mmol, 98.7% ee as determined by CSP-HPLC after derivatisation as per general procedure B). The hemithioester product (29) was suspended in aq. NH$_3$ (3 mL) and stirred at room temperature for 4 h. The reaction was then diluted with CH$_2$Cl$_2$ (10.0 mL) and H$_2$O (5.0 mL) and transferred to a separating funnel. The organic and aqueous layers were separated and the aqueous layer was extracted with CH$_2$Cl$_2$ (2×10.0 mL). The combined organic layers were then dried over MgSO$_4$ and the solvent removed under reduced pressure affording the 'fast reacting' (S)-thiol enantiomer (62.4 mg, 0.35 mmol, 95.5% ee as determined by CSP-HPLC after derivatisation as per general procedure B) after flash chromatography. Conversion=50.8%, S Factor=226.

The aqueous layer was then acidified by addition of HCl (8 N) and extracted with EtOAc (5×15 mL). The combined organic phases were then dried over magnesium sulphate and the solvent was removed under reduced pressure to afford the desired hemiamide as a white solid (71.2 mg, 0.38 mmol, 97.0% ee as determined by CSP-HPLC after transformation to the corresponding o-nitrophenoxy ester, as per the procedure reported below).

¹H NMR spectrum of (S)-30 (400 MHz, DMSO-d₆): δ 12.0 (br s, 1H), 7.27 (s, 1H), 6.74 (s, 1H), 2.22-1.91 (m, 5H), 1.66-1.51 (m, 1H), 1.09 (app t, J 6.6, 2H), 0.81 (d, J 6.6, 6H). ¹³C NMR (100 MHz, DMSO-d₆): δ 174.3 (q), 173.9 (q), 43.6, 40.2, 39.2, 30.1, 25.0, 23.2, 23.1. HRMS (m/z): [M+Na]⁺ calcd. for C₉H₁₇NO₃Na 210.1106. found, 210.1114.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of resolving a mixture of stereoisomers of a thiol comprising the step of preferentially acylating one thiol stereoisomer in the presence of a bifunctional organocatalyst; wherein the bifunctional organocatalyst is selected from the group consisting of:

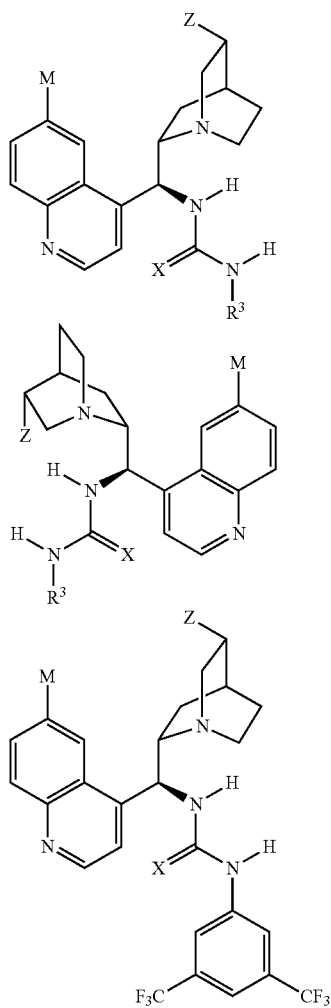

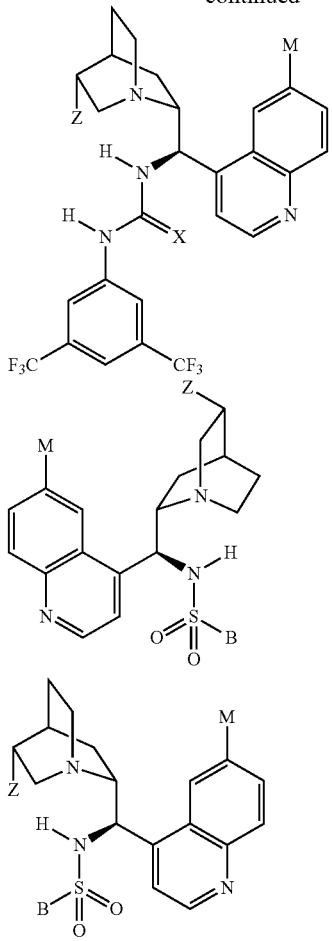

wherein X can be O or S;

Z can be $C_1$ to $C_5$ carbon chain optionally comprising at least one C—C unsaturated bond, and optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_3$ can be $C_1$-$C_{15}$ alkyl, $C_5$-$C_{15}$ aryl ring, or $C_5$-$C_{15}$ heteroaryl ring which may be optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

2. A method according to claim 1 wherein the mixture of stereoisomers of the thiol is an enantiomeric mixture of the thiol.

3. A method according to claim 1 wherein the thiols are selected from the group consisting of primary thiols and secondary thiols.

4. A method according to claim 1 wherein the bifunctional organocatalyst comprises a cinchona alkaloid.

5. A method according to claim 4 wherein the cinchona alkaloid is substituted with urea, thiourea or sulfonamide functional group.

6. A method according to claim 1 wherein the step of acylating the thiol comprises reacting the thiol with an organic anhydride.

7. A method according to claim 6 wherein the organic anhydride is selected from the group consisting of:

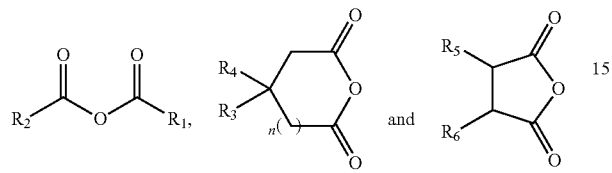

wherein $R_1$ and $R_2$ are the same or different and are selected from the group consisting of $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of halogen, cyano, or $C_1$-$C_5$ fluoroalkyl;

$R_3$ and $R_4$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of halogen, cyano, or $C_1$-$C_5$ fluoroalkyl, such that at least one of $R_3$ and $R_4$ is H;

$R_5$ and $R_6$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of halogen, cyano, or $C_1$-$C_5$ fluoroalkyl; and n is 0-5.

8. A process for the preparation of enantioenriched 3-(aminomethyl)-5-methylhexanoic acid comprising the steps of:
i) preferentially acylating one thiol enantiomer of an enantiomeric mixture of the thiol with 3-isobutylglutaric anhydride in the presence of a bifunctional organocatalyst;
wherein the bifunctional organocatalyst is selected from the group consisting of:

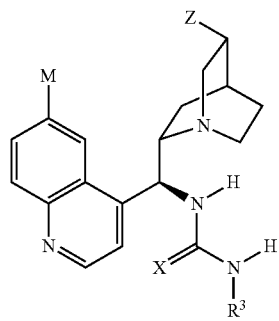

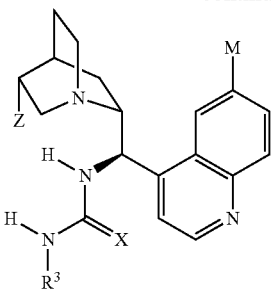

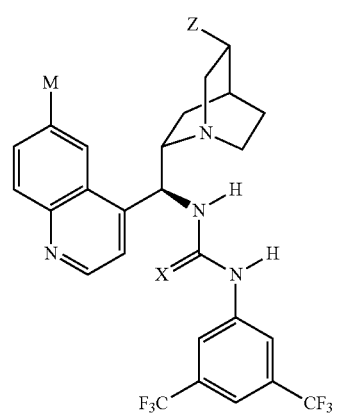

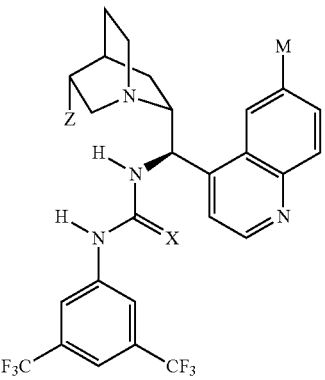

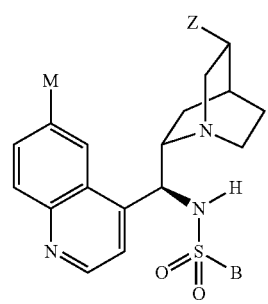

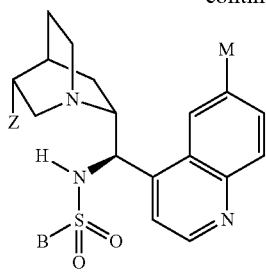

wherein X can be O or S;

Z can be a $C_1$ to $C_5$ carbon chain optionally comprising at least one C—C unsaturated bond, and optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

$R_3$ can be $C_1$-$C_{15}$ alkyl, $C_5$-$C_{15}$ aryl ring, or $C_5$-$C_{15}$ heteroaryl ring which may be optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof;

and ii) converting the thioester functional group into an amine.

9. A process according to claim 8 wherein the step of converting the thioester functional group into an amine comprises:

(a) aminolysis of the thioester functional group to yield an amide; and (b) subjecting the amide product of step (a) to Hofmann rearrangement.

10. A method according to claim 1, wherein the step of acylating the thiol comprises reacting the thiol with an organic anhydride, wherein the organic anhydride is a prochiral anhydride and wherein acylation of the thiol with the prochiral anhydride in the presence of the bifunctional organocatalyst proceeds with desymmetrisation of the prochiral anhydride to afford a thioester.

11. A method according to claim 10 wherein the prochiral anhydride is of the general formula:

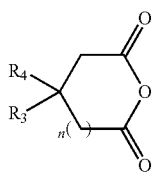

wherein $R_3$ and $R_4$ are the same or different and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of halogen, cyano, or $C_1$-$C_5$ fluoroalkyl, such that at least one of $R_3$ and $R_4$ is H; and n is 1.

12. A method according to claim 1, wherein the step of acylating the thiol comprises reacting the thiol with an organic anhydride, wherein the organic anhydride is a meso anhydride and wherein acylation of the thiol with the meso anhydride in the presence of the bifunctional organocatalyst proceeds with desymmetrisation of the meso anhydride to afford a thioester; wherein the thioester is at least one of enantiomerically or diastereomerically enriched.

13. A method according to claim 12, wherein the meso anhydride is of the general formula:

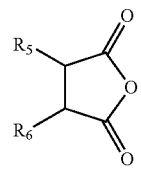

wherein $R_5$ and $R_6$ are the same and are selected from the group consisting of H, $C_1$-$C_{20}$ alkyl, $C_3$-$C_{20}$ cycloalkyl, $C_5$-$C_{20}$ aryl, $C_5$-$C_{20}$ heteroaryl and combinations thereof, optionally substituted with at least one of halogen, cyano, or $C_1$-$C_5$ fluoroalkyl.

14. A method according to claim 10 wherein the thioester is at least one of enantiomerically or diastereomerically enriched.

15. A method according to claim 11 wherein the thioester is at least one of enantiomerically or diastereomerically enriched.

16. A method according to claim 10 wherein the thiols are selected from the group consisting of primary thiols and secondary thiols.

17. A method according to claim 11 wherein the thiols are selected from the group consisting of primary thiols and secondary thiols.

18. A method according to claim 1 wherein the bifunctional organocatalyst is selected from the group consisting of:

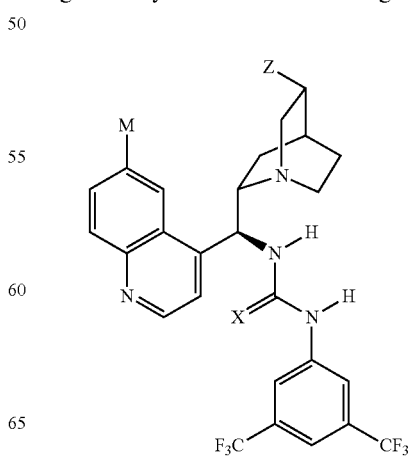

-continued

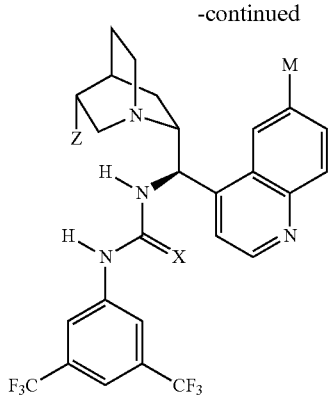

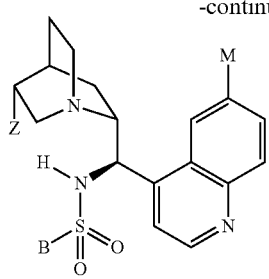

-continued

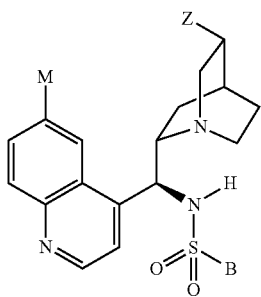

wherein X can be O or S;

Z can be a $C_1$ to $C_5$ carbon chain optionally comprising at least one C—C unsaturated bond, and optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide and combinations thereof;

M can be H, OH, or OMe;

B can be $C_1$-$C_{15}$ alkyl, $C_3$-$C_{15}$ cycloalkyl, $C_5$-$C_{15}$ aryl, $C_5$-$C_{15}$ heteroaryl or combinations thereof, optionally substituted one or more times with at least one of halogen, cyano, $CF_3$, $NO_2$, $C_1$-$C_5$ ketone, $C_1$-$C_5$ ester, $C_1$-$C_{10}$ amide, $C_1$-$C_5$ sulfone, $C_1$-$C_5$ sulfoxide, $C_1$-$C_5$ alkyl and combinations thereof.

* * * * *